(12) United States Patent
Rosenberg et al.

(10) Patent No.: US 10,471,236 B2
(45) Date of Patent: Nov. 12, 2019

(54) SYSTEM FOR ANCHORING MEDICAL DEVICES

(71) Applicant: INTERRAD Medical, Inc., Plymouth, MN (US)

(72) Inventors: Michael S. Rosenberg, Eagan, MN (US); Mark R. Christianson, Plymouth, MN (US); Kyle P. Taylor, Brooklyn Park, MN (US); Andrew T. Forsberg, Plymouth, MN (US)

(73) Assignee: INTERRAD Medical, Inc., Plymouth, MN (US)

( * ) Notice: Subject to any disclaimer, the term of this patent is extended or adjusted under 35 U.S.C. 154(b) by 88 days.

(21) Appl. No.: 15/897,908

(22) Filed: Feb. 15, 2018

(65) Prior Publication Data

US 2018/0169387 A1    Jun. 21, 2018

Related U.S. Application Data

(60) Continuation of application No. 15/016,984, filed on Feb. 5, 2016, now Pat. No. 9,919,134, which is a continuation of application No. 14/134,590, filed on Dec. 19, 2013, now Pat. No. 9,283,355, which is a division of application No. 13/542,080, filed on Jul. 5, 2012, now Pat. No. 8,628,511, which is a division of application No. 12/163,539, filed on Jun. 27, 2008, now Pat. No. 8,235,948.

(51) Int. Cl.
*A61M 25/04* (2006.01)
*A61M 25/02* (2006.01)

(52) U.S. Cl.
CPC ............ *A61M 25/04* (2013.01); *A61M 25/02* (2013.01); *A61M 2025/028* (2013.01); *A61M 2025/0246* (2013.01); *A61M 2025/0286* (2013.01); *Y10S 128/26* (2013.01)

(58) Field of Classification Search
CPC ...... A61M 25/01; A61M 25/02; A61M 25/04; A61M 2025/0246; A61M 2025/028; A61M 2025/0286; A61M 2210/04; Y10S 128/26
See application file for complete search history.

(56) References Cited

U.S. PATENT DOCUMENTS

| 2,525,398 A | 10/1950 | Collins |
| 3,059,645 A | 10/1962 | Hasbrouck et al. |
| 3,108,595 A | 10/1963 | Overment |

(Continued)

FOREIGN PATENT DOCUMENTS

| EP | 0116526 | 8/1984 |
| EP | 0341039 | 11/1989 |

(Continued)

OTHER PUBLICATIONS

European Search Report in Application No. EP 09770944.8, dated Jul. 26, 2011, 10 pages.

(Continued)

*Primary Examiner* — Shefali D Patel
(74) *Attorney, Agent, or Firm* — Fish & Richardson P.C.

(57) ABSTRACT

Some embodiments of a medical device anchor system include an anchor device that receives a catheter (or other medical instrument) and secures the catheter in place relative to a skin penetration point. In some embodiments, the anchor device can secure the catheter in an operative position relative to the skin penetration point without the use of sutures or skin tapes.

20 Claims, 15 Drawing Sheets

(56) References Cited

U.S. PATENT DOCUMENTS

| | | |
|---|---|---|
| 3,176,690 A | 4/1965 | H'Doubler |
| 3,630,195 A | 12/1971 | Santomieri |
| 3,677,250 A | 7/1972 | Thomas |
| 3,717,151 A | 2/1973 | Collett |
| 3,834,380 A | 9/1974 | Boyd |
| 3,856,009 A | 12/1974 | Winnie |
| 3,896,527 A | 7/1975 | Miller et al. |
| 3,938,529 A | 2/1976 | Gibbons |
| 4,043,346 A | 8/1977 | Mobley et al. |
| 4,114,618 A | 9/1978 | Vargas |
| 4,164,943 A | 8/1979 | Hill et al. |
| 4,248,224 A | 2/1981 | Jones |
| 4,309,994 A | 1/1982 | Grunwald |
| 4,397,647 A | 8/1983 | Gordon |
| 4,474,569 A | 10/1984 | Newkirk |
| 4,592,356 A | 6/1986 | Gutierrez |
| 4,645,492 A | 2/1987 | Weeks |
| 4,665,906 A | 5/1987 | Jervis |
| 4,799,495 A | 1/1989 | Hawkins et al. |
| 4,804,359 A | 2/1989 | Grunwald et al. |
| 4,813,930 A | 3/1989 | Elliott |
| 4,936,823 A | 6/1990 | Colvin et al. |
| 4,986,810 A | 1/1991 | Semrad |
| 5,041,085 A | 8/1991 | Osborne et al. |
| 5,067,957 A | 11/1991 | Jervis |
| 5,122,122 A | 6/1992 | Allgood |
| 5,190,546 A | 3/1993 | Jervis |
| 5,256,146 A | 10/1993 | Ensminger et al. |
| 5,267,960 A | 12/1993 | Hayman et al. |
| 5,312,337 A | 5/1994 | Flaherty et al. |
| 5,344,439 A | 9/1994 | Otten |
| 5,378,239 A | 1/1995 | Termin et al. |
| 5,456,671 A | 10/1995 | Bierman |
| 5,496,277 A | 3/1996 | Termin et al. |
| 5,540,648 A | 7/1996 | Yoon |
| 5,578,013 A | 11/1996 | Bierman |
| 5,597,378 A | 1/1997 | Jervis |
| 5,599,311 A | 2/1997 | Raulerson |
| 5,681,288 A | 10/1997 | Schlitt |
| 5,688,247 A | 11/1997 | Haindl et al. |
| 5,702,371 A | 12/1997 | Bierman |
| 5,707,362 A | 1/1998 | Yoon |
| 5,722,959 A | 3/1998 | Bierman |
| 5,728,133 A | 3/1998 | Kontos |
| 5,741,234 A | 4/1998 | Aboul-Hosn |
| 5,746,720 A | 5/1998 | Stouder, Jr. |
| 5,755,697 A | 5/1998 | Jones et al. |
| 5,769,821 A | 6/1998 | Abrahamson et al. |
| 5,800,402 A | 9/1998 | Bierman |
| 5,810,781 A | 9/1998 | Bierman |
| 5,827,230 A | 10/1998 | Bierman |
| 5,833,667 A | 11/1998 | Bierman |
| 5,857,999 A | 1/1999 | Quick et al. |
| 5,921,965 A | 7/1999 | Blei |
| 5,928,266 A | 7/1999 | Kontos |
| 5,944,732 A | 8/1999 | Raulerson et al. |
| 5,947,931 A | 9/1999 | Bierman |
| 5,971,960 A | 10/1999 | Flom et al. |
| 5,989,265 A | 11/1999 | Bouquet De La Joliniere et al. |
| 6,090,072 A | 7/2000 | Kratoska et al. |
| 6,213,979 B1 | 4/2001 | Bierman |
| 6,290,676 B1 | 9/2001 | Bierman |
| 6,413,240 B1 | 7/2002 | Bierman et al. |
| 6,447,485 B2 | 9/2002 | Bierman |
| 6,540,693 B2 | 4/2003 | Burbank et al. |
| 6,572,588 B1 | 6/2003 | Bierman et al. |
| 6,582,403 B1 | 6/2003 | Bierman et al. |
| 6,663,600 B2 | 12/2003 | Bierman et al. |
| 6,679,851 B2 | 1/2004 | Burbank et al. |
| 6,695,861 B1 | 2/2004 | Rosenberg et al. |
| 6,770,055 B2 | 8/2004 | Bierman et al. |
| 6,786,892 B2 | 9/2004 | Bierman |
| 6,827,705 B2 | 12/2004 | Bierman |
| 6,837,875 B1 | 1/2005 | Bierman |
| 6,896,665 B2 | 5/2005 | Picha et al. |
| 6,929,625 B2 | 8/2005 | Bierman |
| 6,958,044 B2 | 10/2005 | Burbank et al. |
| 6,972,003 B2 | 12/2005 | Bierman et al. |
| 7,018,362 B2 | 3/2006 | Bierman et al. |
| 7,056,286 B2 | 6/2006 | Ravenscroft et al. |
| 7,087,069 B2 | 8/2006 | Petrovic et al. |
| 7,247,150 B2 | 7/2007 | Bierman |
| 7,273,468 B2 | 9/2007 | Bedell |
| 8,235,948 B2 | 8/2012 | Rosenberg |
| 8,628,511 B2 | 1/2014 | Rosenberg |
| 2001/0056261 A1 | 12/2001 | Lerman et al. |
| 2002/0068898 A1 | 6/2002 | McGuckin, Jr. et al. |
| 2002/0068899 A1 | 6/2002 | McGuckin, Jr. et al. |
| 2002/0165489 A1 | 11/2002 | McGuckin, Jr. et al. |
| 2005/0043685 A1 | 2/2005 | Schinkel-Fleitmann |
| 2005/0137498 A1 | 6/2005 | Sakal et al. |
| 2005/0187578 A1 | 8/2005 | Rosenberg et al. |
| 2005/0273058 A1 | 12/2005 | Bierman |
| 2007/0078397 A1 | 4/2007 | Weststrate |
| 2007/0225651 A1 | 9/2007 | Rosenberg et al. |
| 2007/0260220 A1 | 11/2007 | Goedje et al. |
| 2012/0271238 A1 | 10/2012 | Rosenberg |
| 2014/0107583 A1 | 4/2014 | Rosenberg |

FOREIGN PATENT DOCUMENTS

| | | |
|---|---|---|
| EP | 1852140 | 11/2007 |
| WO | WO 91/15254 | 10/1991 |
| WO | WO 98/53872 | 12/1998 |
| WO | WO 03/51447 | 6/2003 |
| WO | WO 04/26152 | 4/2004 |
| WO | WO 05/39419 | 5/2005 |
| WO | WO 05/102438 | 11/2005 |
| WO | WO 07/103999 | 9/2007 |

OTHER PUBLICATIONS

European Search Report in Application No. EP 13181068.1 dated Sep. 19, 2013, 7 pages.
International Preliminary Report on Patentability for PCT/US2009/048474 dated Jan. 13, 2011, 6 pages.
International Search Report and Written Opinion for PCT/US2009/048474, dated Jan. 22, 2010, 12 pages.
Johnson & Johnson web page printout, "The EndoANCHOR Comparative Summary" printed Sep. 13, 2005, 2 pages.
Johnson & Johnson web page printout, "The EndoANCHOR Features and Benefits" printed Sep. 13, 2005, 2 pages.
Johnson & Johnson web page printout, "The EndoANCHOR Firing Sequences" printed Sep. 13, 2005, 2 pages.
U.S. Appl. No. 60/412,453, filed Sep. 20, 2002, Claude et al., 9 pages.
Web Page Printout of Statlock Device, (publicly available prior to Jun. 27, 2008), 2 pages.

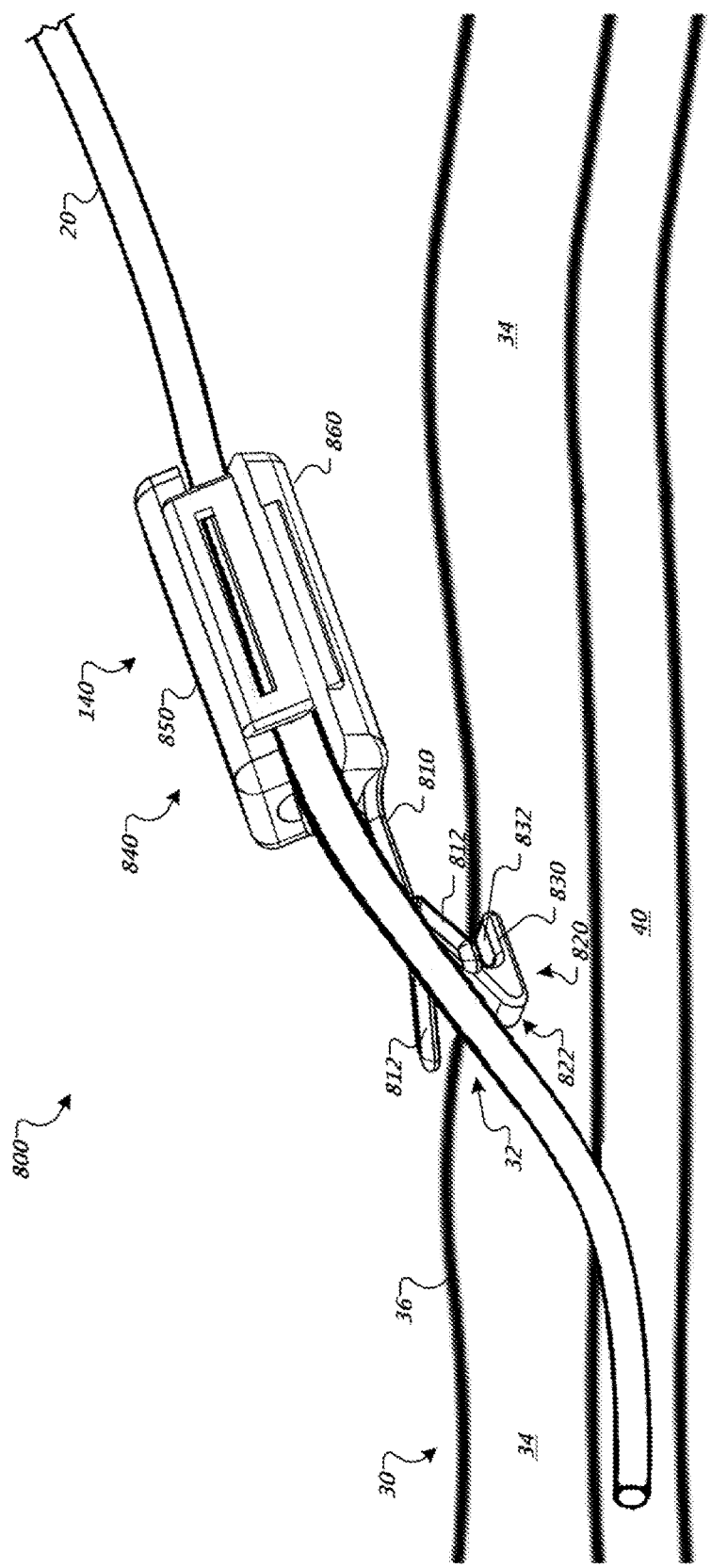

SYSTEM FOR ANCHORING MEDICAL DEVICES

CROSS-REFERENCE TO RELATED APPLICATIONS

This is a continuation of U.S. patent application Ser. No. 15/016,984 filed on Feb. 5, 2016, which is a continuation of U.S. patent application Ser. No. 14/134,590 filed Dec. 19, 2013, which is a divisional of U.S. patent application Ser. No. 13/542,080 filed on Jul. 5, 2012 by Rosenberg et al., which is a divisional of U.S. patent application Ser. No. 12/163,539 filed on Jun. 27, 2008 by Rosenberg et al. The contents of these previous applications are fully incorporated herein by reference.

TECHNICAL FIELD

This document relates to an anchor device, such as a device for use in securing the position of a catheter or other medical instrument.

BACKGROUND

Venous, arterial, and body fluid catheters are commonly used by physicians. For example, such catheters may be used to gain access to the vascular system for dialysis, for introducing pharmaceutical agents, for nutrition or fluids, for hemodynamic monitoring, and for blood draws. Alternatively, catheters can be used for drainage of fluid collections and to treat infection. Following introduction into the patient, the catheter is secured to the patient. In conventional practice, the catheter is commonly secured to the patient using an adhesive tape on the skin or by suturing a catheter hub to the patient's skin.

SUMMARY

Some embodiments of a medical device anchor system include an anchor device that receives a medical instrument (such as a catheter or the like) and secures the instrument in place relative to a skin penetration point. In some circumstances, the anchor device can be designed to be inserted through the skin penetration point that is already occupied by the medical instrument, thus allowing the anchor device to be used after medical instrument is already in place and reducing the need for a second penetration point for the anchor device. In particular embodiments, the anchor device may have a multi-piece design that can simplify post-operative removal and reduce trauma to surrounding tissue near the skin penetration point. For example, the anchor device can be separated into at least two portions prior to removal from the skin penetration point. In these circumstances, the separable portions may each include a subcutaneous anchor, and each anchor can be removed from the skin penetration point independently of the other in a manner that reduces the likelihood of damage to the tissue surrounding the skin penetration point.

In some embodiments, an anchor device may include a retainer body to releasably couple to a catheter. The retainer body may be separable into a first body portion and a second body portion. The device may also include first and second anchors that extend distally from the retainer body. Each anchor may comprise a flexible tine that is deployable in a subcutaneous region to secure the retainer body relative to a penetration point. The first anchor may be coupled to the first body portion, and the second anchor may be coupled to the second body portion. The first and second body portions may be releasably coupled together so that the first and second anchors are collectively deployable into the subcutaneous region. Also, the first and second body portions may be separable from one another when the first and second anchors are deployed in the subcutaneous region so that the first anchor is removable from the subcutaneous region independent of the second anchor.

Particular embodiments include an anchor system for securing the position of a medical instrument. The system may include a medical instrument that is insertable into a skin penetration point. Also the system may include an anchor device comprising a retainer body and one or more subcutaneous anchors. The retainer body may releasably secure with the medical instrument when the medical instrument is inserted into the skin penetration point. The one or more anchors may extend distally from the retainer body and toward the skin penetration point when the medical instrument is inserted into the skin penetration point. Each anchor may comprise a tine that deploys in a subcutaneous region to secure the retainer body relative to the skin penetration point.

In certain embodiments, a method of anchoring a catheter may include advancing a catheter though a skin penetration point. The method may also include directing an anchor device toward the skin penetration point that is occupied by a portion of the catheter. The anchor device may comprise a retainer body to releasably couple to an external portion of the catheter arranged outside the body, and at least one anchor extending distally from the retainer body. The method may further include inserting the anchor through the skin penetration point that is occupied by the catheter so that at least a portion of the anchor is deployed in a subcutaneous region proximate the skin penetration point.

These and other embodiments may provide one or more of the following advantages. First, some embodiments of an anchor system can retain a medical instrument in a desired position relative to a skin penetration point without necessarily requiring sutures or skin adhesives. Second, in some embodiments, an anchor device can include a retention portion that readily mates with a medical instrument (such as a catheter) and at least one anchor extending distally from the retention portion to engage the skin penetration point as the medical instrument. Third, the anchor device can include one or more anchors configured to deploy in a subcutaneous region under the skin proximate to the skin penetration point of the medical instrument. In such circumstances, the anchors may be inserted through the skin penetration point in a manner that reduces the likelihood of trauma to the surround skin tissue. Fourth, in some embodiments, the anchor device may include multiple components that are separable from one another before the anchor device is removed from the skin. For example, the anchor device may include a first portion and a second portion that are coupled together (as the fully assembled anchor device) during insertion into the skin penetration point, but the first and second portions can be readily separated from one another to facilitate removal from the skin. Accordingly, the anchors 120a and 120b (including the tines 130a and 130b) can collectively penetrate into the subcutaneous region 34 as part of the assembled device 100, and may be separately and individually withdrawn from penetration point 34 during the removal process. Such a configuration can permit the first and second portions to be maneuvered in a manner that reduces the likelihood of causing damage to the skin during removal of the anchors.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 10 is a perspective view of an alternative embodiment of the anchor device, having an anchor tab, with a portion of the device located in a subcutaneous region.

Like reference symbols in the various drawings indicate like elements.

DETAILED DESCRIPTION OF ILLUSTRATIVE EMBODIMENTS

Figure 1:
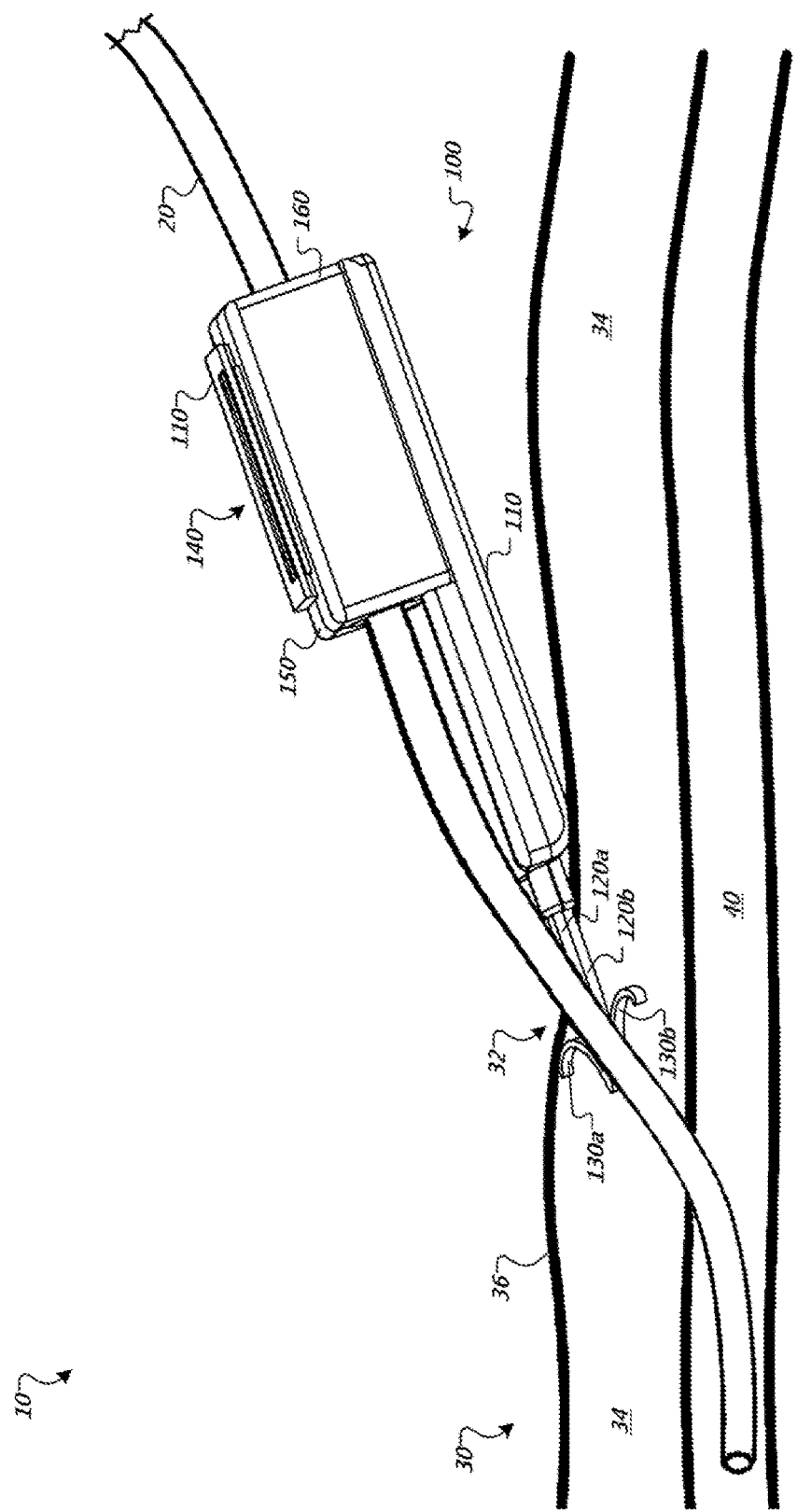
FIG. 1 is a perspective view of an anchor device with a portion of the device located in a subcutaneous region, in accordance with some embodiments.

Referring to FIG. 1, some embodiments of a medical device anchor system 10 include an anchor device 100 that releasably retains a medical instrument 20 (e.g., depicted as a catheter in this embodiment) in an operative position relative to a skin penetration point 32. The anchor device 100 may include a retainer body 110 that receives the medical instrument 20 and can releasably engage with an outer surface of the medical instrument 20. The medical instrument 20 extends from the retainer body 110 and through the penetration point 32 in the patient's skin 30 (e.g., through an incision or the like), while the retainer body 110 remains outside of the skin 30. As described in more detail below, the anchor device 100 can secure the catheter 20 in the operative position relative to the penetration point 32 without necessarily requiring sutures or adhesive tapes bonded to the skin. For example, the anchor device 100 can include one or more anchors 120a and 120b that extend distally from the retainer body 110 so as to penetrate through the same skin opening as the medical instrument 20. The anchors 120a and 120b can include tines 130a and 130b that, after insertion, reside in a subcutaneous region 34 (e.g., a region under the skin 30 that may comprise a fatty tissue layer) so as to secure the position of the anchor device 100—and the medical instrument 20 retained therein—relative to the penetration point 32.

Figure 2A:
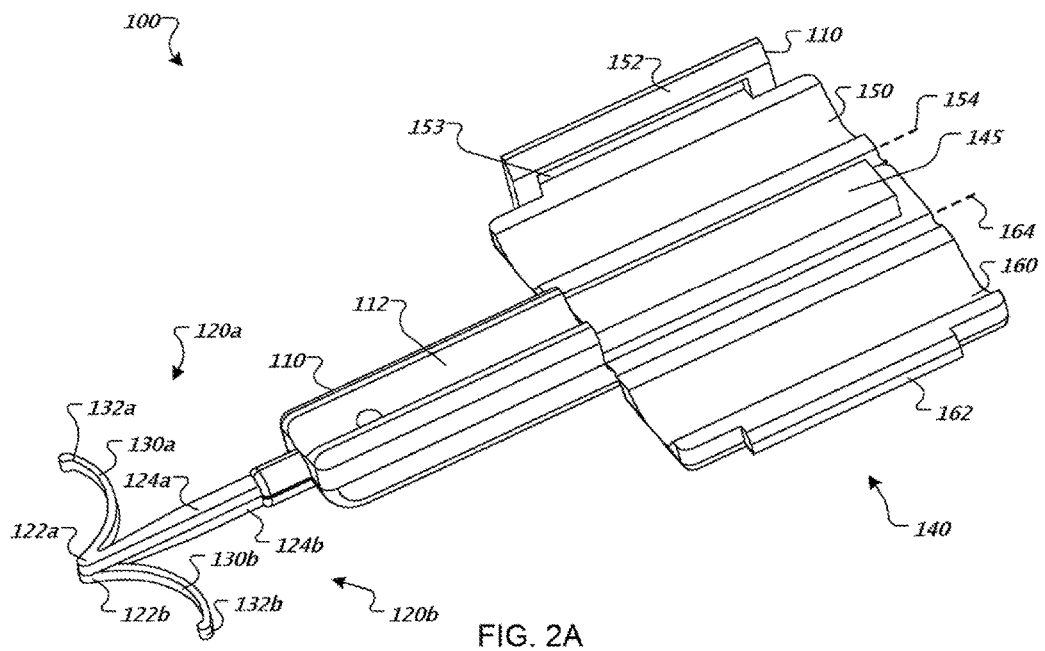
FIGS. 2A-2B are perspective views of the anchor device of FIG. 1 with the medical device retention portion in open and closed positions, respectively.

In some embodiments, the medical instrument 20 can include a catheter to be inserted through the penetration point 32 of the skin 30 as part of a medical procedure. For example, in the embodiment depicted in FIG. 1, a central venous catheter 20 can be inserted into a percutaneous opening surgically formed in the skin (e.g., penetration point 32), to the underside of the skin 30, and into a vein 40 to provide vascular access for delivering medications or minimally invasive devices into a patient. As described in greater detail below, after placement of the catheter 20, the anchor device 100 (arranged in the open configuration as shown in FIG. 2A) can be inserted into the penetration point 32 such that the tips 122a and 122b (FIG. 2A) of the anchors 120a and 120b enter the skin 30 through the penetration point 32. As the anchor device 10 is inserted through the penetration point 32, the tines 130a and 130b are stressed to flex against anchor bodies 124a and 124b (FIG. 2A) to pass through the penetration point with reduced trauma to the surrounding skin tissue. As the anchors 120a and 120b are collectively advanced through the penetration point 32, the tines 130a and 130b are moved beneath the dermal layers 36 (e.g., the dermis, the epidermis, etc.) of the skin 30. When the tines 130a and 130b reach the subcutaneous region 34, the tines 130a and 130b can return toward an unstressed shape (FIG. 2A) and thereby deploying in the subcutaneous region 34. As shown in FIG. 1, the anchors 120a and 120b may be designed such that the tines 130a and 130b include a curvature that abuts against the underside of the dermal layers 36 in a manner that reduces the likelihood of the tine tips 132a and 132b (FIG. 2A) puncturing the underside of the dermal layers 36. When the tines 130a and 130b of the anchors 120a and 120b are deployed in the subcutaneous region 34, the anchor device 100 can be secured to the patient without the retainer body 110 penetrating though the skin 30 of the patient and without necessarily requiring sutures or adhesive tapes bonded to the skin 30.

Figure 2B:
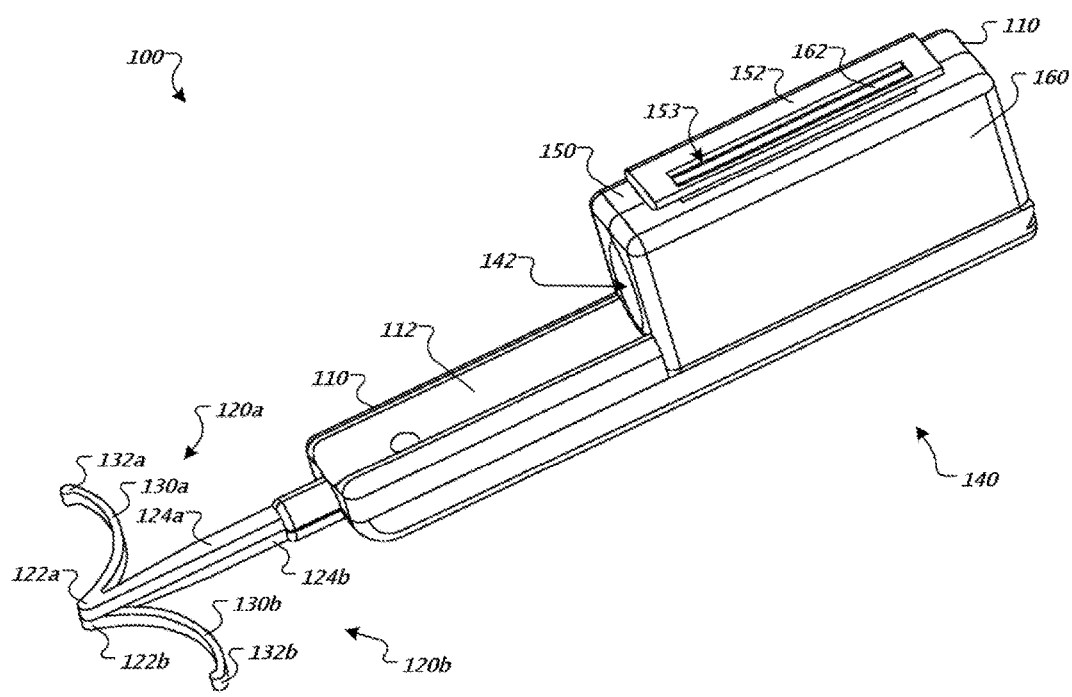

Referring now to FIGS. 1 and 2A-B, the retainer body 110 can include an instrument retention portion 140 used to secure the catheter 20 (or other medical instrument) relative to the skin penetration point 32. For example, after the catheter 20 is delivered into the targeted vein 40 (or other bodily lumen) and after the anchors 120a and 120b are deployed in the subcutaneous region 34, the catheter 20 can be pressed against a foam adhesive pad 145 (FIG. 2A) to temporarily secure the catheter relative to the retention portion 140. From there, the anchor device 100 can be transitioned from the open configuration (shown in FIG. 2A) to a closed configuration (shown in FIGS. 1 and 2B) to thereby secure the catheter 20 with the retention portion 140. As described in greater detail below, the catheter retention portion 140 of the retainer body 110 can include retention members 150 and 160 (FIG. 2A) that can be transitioned from the open configuration to the closed configuration to press against and releasably retain the catheter 20 in a desired position. In this embodiment, the retention members 150 and 160 comprise adjustable wing include locking tabs 152 and 162 (FIG. 2A) that positively engage one another to releasably lock the retention portion 140 in the closed position.

In some embodiments, the anchor device 100 can include features that facilitate separation from the catheter 20 and removal from the skin 30 in a manner that reduces the likelihood of trauma to the skin 30 surrounding penetration point 32. For example, tabs 152 and 162 may be disengaged allowing the retention members 150 and 160 to shift away from one another and return to the open configuration shown in FIG. 2A. Once the retention portion 140 is opened, the catheter 20 can be separated from the anchor device 100 (e.g., by lifting the catheter 20 from the adhesive pad 145. As such, the catheter 20 can be moved independently from the anchor device 100, for example, to withdraw the catheter 20 from the patient while the anchor device 100 remains secured to the skin 30. In some embodiments, the anchor device 100 can include separable portions that can be disassembled prior to removal of the anchors 120a and 120b from the subcutaneous region 34. For example, in this embodiment, the anchor device 100 comprises an assembly of two pieces 101a and 101b (FIGS. 5A-B) that can separate from one another to facilitate removal of the tine 130a independent of the other tine 130b. Such a configuration permits the anchors 120a and 120b to be maneuvered in a manner that reduces the likelihood of the tines 130a and 130b causing damage to the skin 30 during removal.

Referring now to FIGS. 2A and 2B, some embodiments of the anchor device 100 can include structures designed to mate with portions of the medical instrument 20 to be retained by the anchor device 100. For example, in this embodiment the, retainer body 110 defines a channel 112 that extends longitudinally from the retention portion 140 toward the anchors 120a and 120b. The channel 112 can be configured to complement an outer surface of the catheter 20 or other medical instrument to be anchored by the device 100. For example, during installation of the anchor device 100, the channel 112 can be guided longitudinally along the catheter 20 so that the anchors 120a and 120b are directed toward the penetration point 32 through which the catheter 20 passes. In addition, the channel 112 can be aligned with a longitudinal opening 142 defined by the retainer wings 150 and 160 when arranged in the closed configuration (FIG. 2B). As such, the catheter 20 can extend through the longitudinal opening 142 and along the channel 112 when the anchors 120a and 120b are deployed under the skin 30. As previously described, some embodiments of the anchor device 100 may include the adhesive pad 145 to temporarily hold the catheter 20 or other medical instrument. In those embodiments, the adhesive pad 145 may be arranged longitudinally adjacent to the channel 112 so that the catheter 20 or other medical instrument can be readily pressed against the adhesive pad 145 when the catheter 20 or other medical instrument extends along the channel 112. The surface of the pad 145 can include a releasable adhesive that can temporarily retain the catheter 20 in a desired position relative to the retainer body 110 and thereafter permit separation of the catheter 20 from the device 100 (e.g., by peeling the catheter 20 away from the pad 145). In this example, the releasable adhesive on the pad can be selected to provide a predetermined amount of holding force that will maintain the catheter 20 or other medical device in place, but will not damage the catheter 20 or other medical device upon separation.

It should be understood from the description herein that the retention members 150 and 160 can be used in addition to, or as an alternative to, the adhesive pad 145. In the depicted embodiment, the adhesive pad 145 serves as a supplement to the retention members 150 and 160 that releasably secure the catheter 20 or other medical device to the anchor device 100. For example, after a catheter has been positioned such that it is in contact with and releasably secured to the adhesive pad 145, force can be applied to the retention members 150 and 160 such that they pivot around axes 154 and 164 toward the closed configuration (FIG. 2B). As the retention members 150 and 160 transition toward the closed configuration, the tabs 152 and 162 move closer to one another. When the tab 162 engages the complementary tab 152 (e.g., in this embodiment, the tab 162 can "snap" into the slot 153), the retention members 150 and 160 are releasably secured in the closed configuration (FIG. 2B) so as to apply a holding force to the catheter 20 or medical instrument therein.

Referring now to FIG. 2B, when the retention members 150 and 160 are in the closed position surrounding a medical device, such as the catheter 20 (FIG. 1), the catheter 20 can be retained in a substantially fixed position relative to the anchor device 100. In this embodiment, the retention members 150 and 160 can surround the catheter 20 and apply the holding force to the outer surface of the catheter 20. For example, the retention members 150 and 160 may define the longitudinal opening 142 to have a minor diameter that is slightly smaller than the outer surface of the catheter 20, thereby causing the retention members 150 and 160 to squeeze upon the catheter 20 without damaging or affecting the performance of the catheter 20. In some circumstances, the retention members 150 and 160 can include an adhesive coating or adhesive pads along the inner channels that define the longitudinal opening 142. As such, the adhesive coating or adhesive pads would be compressed against the catheter 20 to releasably secure the catheter within the longitudinal opening 142. In alternative embodiments, the retention members 150 and 160 can surround the catheter 20 without necessarily applying a holding force thereto. For example, the retention members 150 and 160 can guard incidental contact to the catheter 20 or other external forces that might otherwise cause the catheter 20 to prematurely peel away from the adhesive pad 145.

Referring again to FIGS. 2A-B, the retention members 150 and 160 can be separated by disengaging the locking tabs 152 and 162 so as to remove the catheter 20 or other medical instrument that has been secured within the anchor device 100. For example, the retention members 150 and 160 can be separated from each other by applying pressure to the tab 152 such that the tab 152 is displaced enough to allow the tab 162 to exit slot 153, thus allowing the retention members 150 and 160 to return to the open configuration. After the retention members 150 and 160 are shifted to the opened configuration (FIG. 2A), the catheter 20 can be peeled away from the adhesive pad 145 to thereby free the catheter for withdrawal from the skin penetration point 32.

Figure 3A:
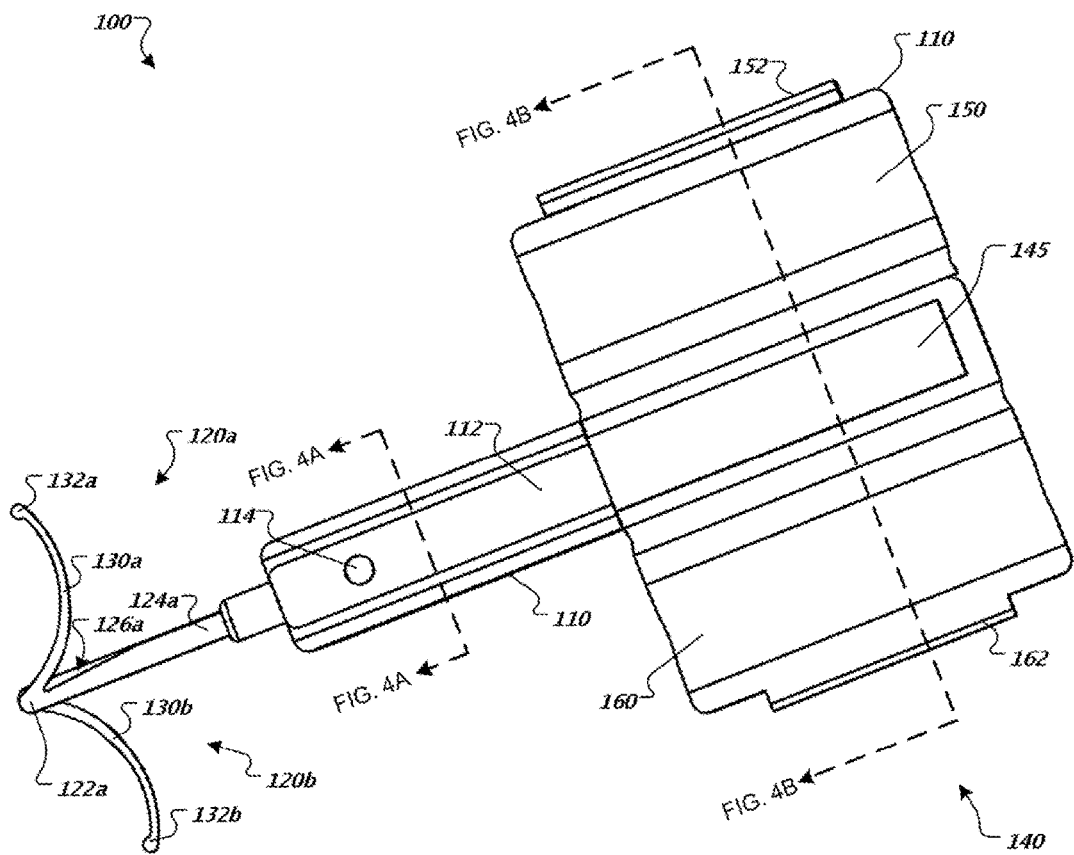
FIG. 3A is a top view of the anchor device of FIG. 1.
Figure 3B:
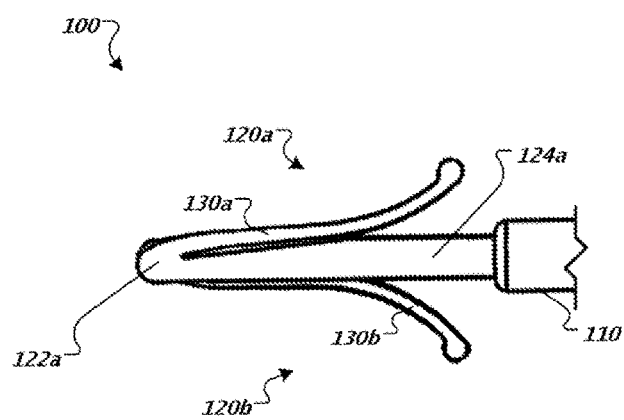
FIG. 3B is a top view of a portion of the anchor device of FIG. 1 with the anchors in a stressed position.

Referring now to FIGS. 3A and 3B, the anchor device 100 can include features that facilitate deploy of the anchors 120a and 120b into the subcutaneous region in a manner that reduces the likelihood of damage to surrounding tissue. For example, in some embodiments, the anchors 120a and 120b may comprise a material that exhibits superelasticity when used in a patient's body. As such, when the tines 130a and 130b of anchors 120a and 120b are stressed by insertion through the skin penetration point 32, the tines 130a and 130b can superelastically flex from an expanded position (FIG. 3A) to a contracted position (FIG. 3B). In this contracted position as shown in FIG. 3B, the tines 130a and 130b may flex against the anchor bodies 124a and 124b. While against the anchor bodies 124a and 124b, the tines 130a and 130b can readily penetrate through the skin penetration point 32 (which may be generally smaller in width than the width occupied by the tines 130a and 130b in a fully expanded state). Such anchor insertion techniques can reduce the damage to the patient's skin 30 during deployment of the anchors 120a and 120b.

In some embodiments, at least portions of the anchors 120a and 120b (including the tines 130a and 130b) may be formed from a length of nitinol wire or from a sheet of nitinol material, which has been processed to exhibit superelasticity below or at about a normal human body temperature, such as below or at about 37 degrees C. The nitinol material may comprise, for example, Nickel Titanium (NiTi), Niobium Titanium (NbTi), or the like. Alternatively, the anchors 120a and 120b may comprise a metal material such as stainless steel (e.g., 304 stainless, 316 stainless, custom 465 stainless, and the like), spring steel, titanium, MP35N, and other cobalt alloys, or the like. In another alternative, the anchors 120a and 120b may be formed from a resilient polymer material. In these embodiments, the anchors 120a and 120b can be formed from a material or materials that allow the tines 130a and 130b to be flexed to a contracted position (e.g., as in FIG. 3B) and can resiliently return to an expanded position (e.g., as in FIG. 3A). To further decrease the insertion profile of the anchors 120a and 120b as they are inserted into the skin 30, the anchor bodies 124a and 124b can include recesses, such as the recess 126a and the corresponding recess (not shown) in the anchor body 124b into which at least a portion of the tines 130a and 130b can inwardly flex. As such, the recesses in the anchor bodies 124a and 124b can at least partially accommodate the tines 130a and 130b when they are flexed into the contracted position, thereby further reducing the insertion profile of the anchors 120a and 120b.

Figure 4A:
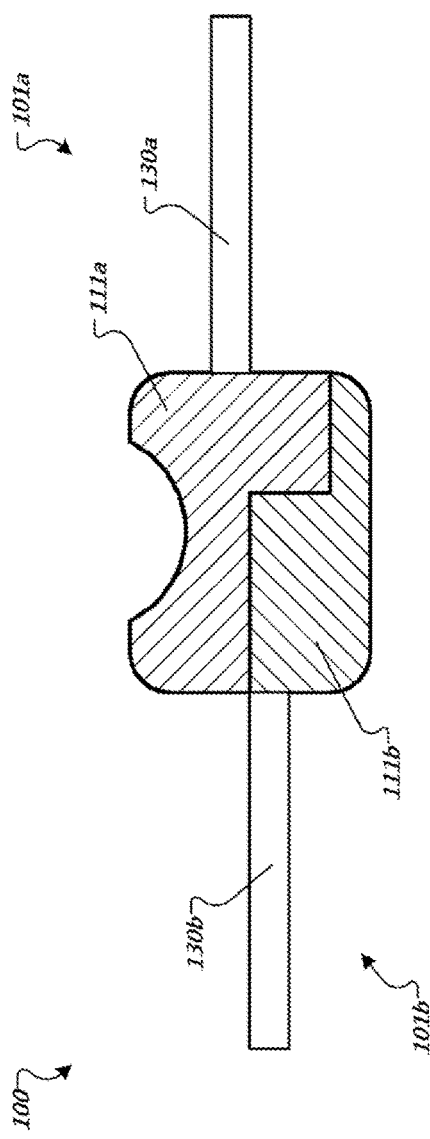
FIGS. 4A-4B are cross-sectional views of the anchor device of FIG. 3A.
Figure 4B:
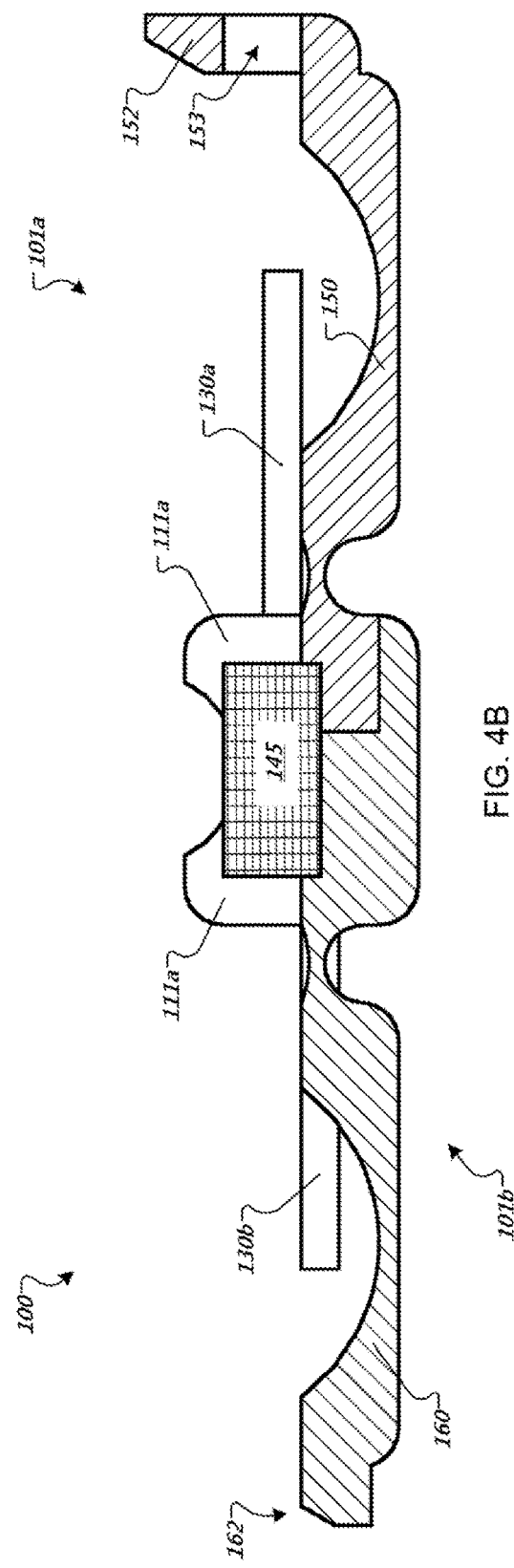

Referring now to FIGS. 4A-4B, the anchor device 100 can be formed from multiple components that are separable from one another after insertion into the patient but prior to removal from the patient. In this embodiment, the anchor device 100 comprises a two-piece design in which a first portion is separable from a second portion so as to facilitate removal of the anchor device 100 from the skin 30. For example, the anchor device 100 can include an upper portion 101a and a lower portion 101b, which can be separated from each other. The upper portion 101a can include an upper main body 111a coupled to the anchor 120a, and the lower portion 101b can include a lower main body 111b coupled to the anchor 120b. To remove the anchor device 100 from a patient, the anchor device 100 can be separated into two components (described in more detail below in connection with FIGS. 5A-5D) allowing for easier removal from a patient. When the upper portion 101a is separated from the lower portion 101b, the anchor 120a can remain attached to the upper main body 111a, while the anchor 120b can remain attached to the lower main body 111b. Thus, the first anchor 120a can be manipulated inside the subcutaneous region 34 (FIG. 1) by a user that handles that upper main body 111a outside the patient's body. Likewise, the second anchor 120b can be manipulated inside the subcutaneous region 34 (FIG. 1) by the user that handles the lower main body 111b. Such manual manipulation of the first and second anchors 120a and 120b can be used to readily remove the tines 130a and 130b through the skin penetration point 32 while reducing the likelihood of trauma to the surround skin tissue.

Referring now to FIGS. 5A-5D, as previously described, the upper portion 101a of the anchor device 100 can be separated from the lower portion 101b before removing the anchors 120a and 120b from the subcutaneous region 34 under the skin 30. In some embodiments, the upper portion 101a and the lower portion 101b are assembled together using a releasable adhesive coating along mating surfaces, one or more score lines or tear lines, or the like. As such, the upper portion 101a and the lower portion 101b are coupled together (as the fully assembled anchor device 100) prior to insertion into the skin penetration point, yet the upper portion 101a and the lower portion 101b can be readily separated after the anchors 120a and 120b are deployed in the subcutaneous region 34. Accordingly, the anchors 120a and 120b (including the tines 130a and 130b) can collectively penetrate into the subcutaneous region 34 as part of the assembled device 100, and may be separately and individually withdrawn from penetration point 34 during the removal process.

At least a portion of the upper portion 101a and the lower portion 101b can comprise a polymer material (e.g., PVC, polypropylene, polystyrene, or the like). In such embodiments, the upper main body 111a and the lower main body 111b can be formed using a molding process in which each of the main bodies 111a and 111b is overmolded around a portion of the associated anchor 120a or 120b. For example, the anchor 120b can include a proximal hub that has a larger cross-sectional area that of the anchor body 124b. During the manufacture of the lower portion 101b, the hub of the anchor body 124b can be positioned inside of an injection mold for the lower main body 111b such that when a polymer is injected to the mold, the polymer material can flow around the hub 128b to thereby couple the lower main body 111b to the anchor 120b. The completed lower body 111b will then at least partially encapsulate the hub 128b, thus securing the anchor 120b to the lower body 111b. It should be understood from the description herein that the anchor 120a can also include a hub so as to be coupled to the upper main body 111a in a similar overmolding process.

Figure 5A:
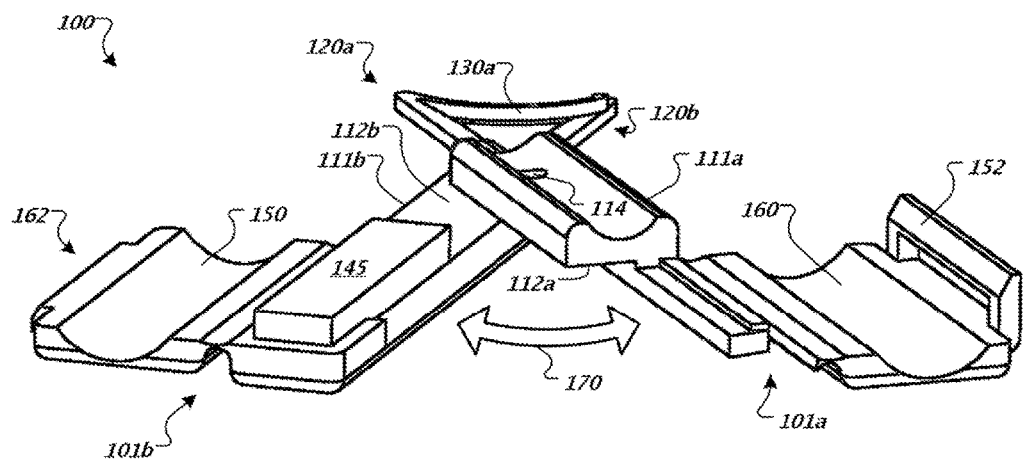
FIGS. 5A-5D are perspective views of the anchor device of FIG. 1, depicting its removal from a subcutaneous region.
Figure 5B:
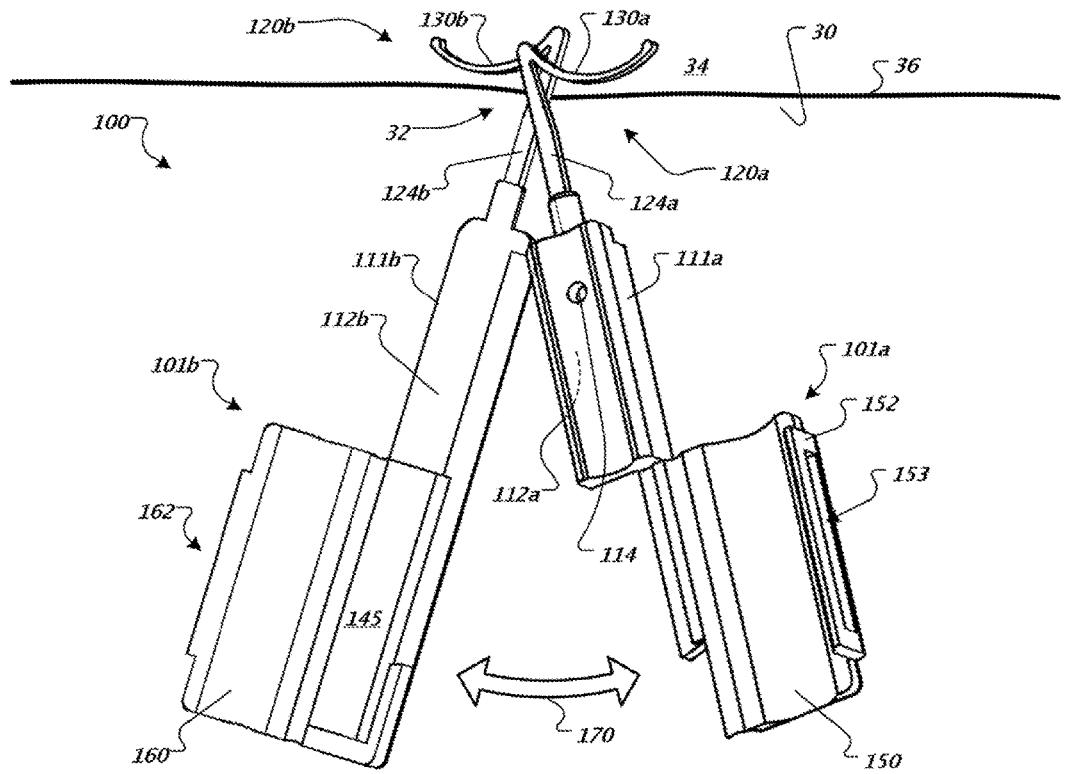

In some embodiments, the upper portion 101a and the lower portion 101b can be manufactured as two separate components that are later joined (e.g., by an adhesive bond, by ultrasonic spot welds, or the like) in a separable manner. In the embodiment depicted in FIGS. 5A-B, the two portions 101a and 101b can be joined in an area adjacent to an orifice 114. For example, during manufacturing of the anchor device 100, the independent portions 101a and 101b can be temporarily held in place (e.g., as in FIG. 2A), while an adhesive is applied into the orifice 114. After the adhesive cures, the portions 101a and 101b can be held together by the cured adhesive alone, in the area proximate the orifice 114 along interfacing surfaces 112a and 112b (FIGS. 5A-B). The adhesive employed in this assembly process can be a releasable adhesive that, during normal usage, retains the upper and lower portions 101a and 101b in the assembled state until the user desires to separate the interfacing surfaces 112a and 112b. At such time, the user may apply a separation force 170 (FIGS. 5A-B) to divide the anchor device 100 into the two separate portions 101a and 101b. In addition or in the alternative to the releasable adhesive, the upper and lower portions 101a and 101b may include plastic spot welds, frangible portions, or other releasable structures at interfacing regions to retain the portions 101a and 101b in the assembled state (FIG. 2A).

Figure 5C:
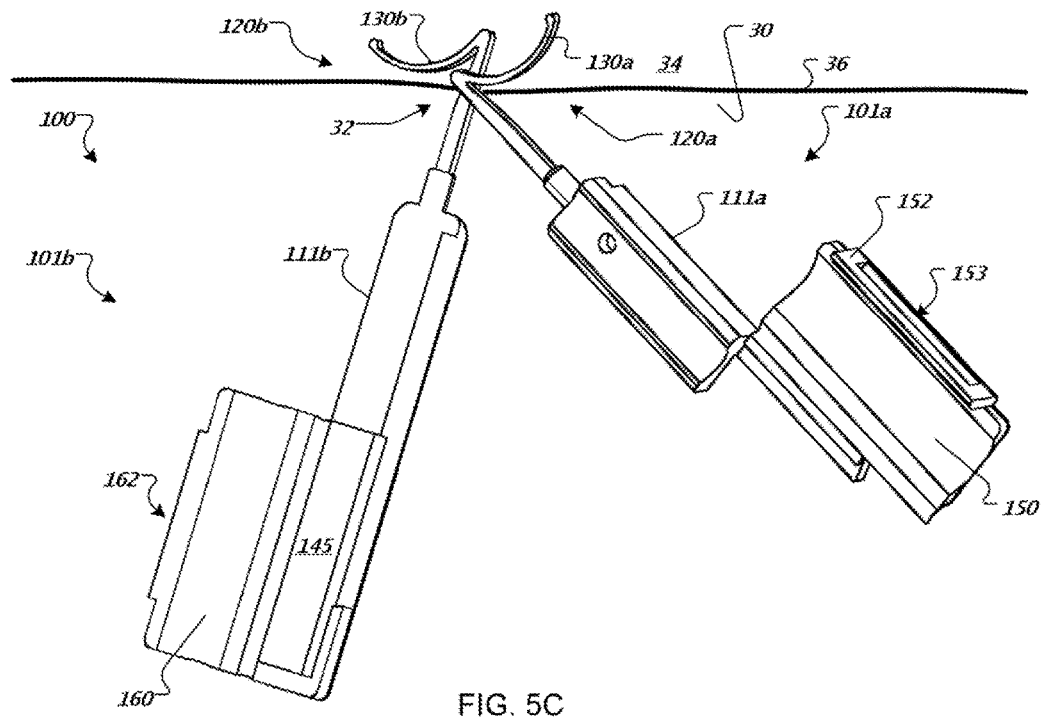
Figure 5D:
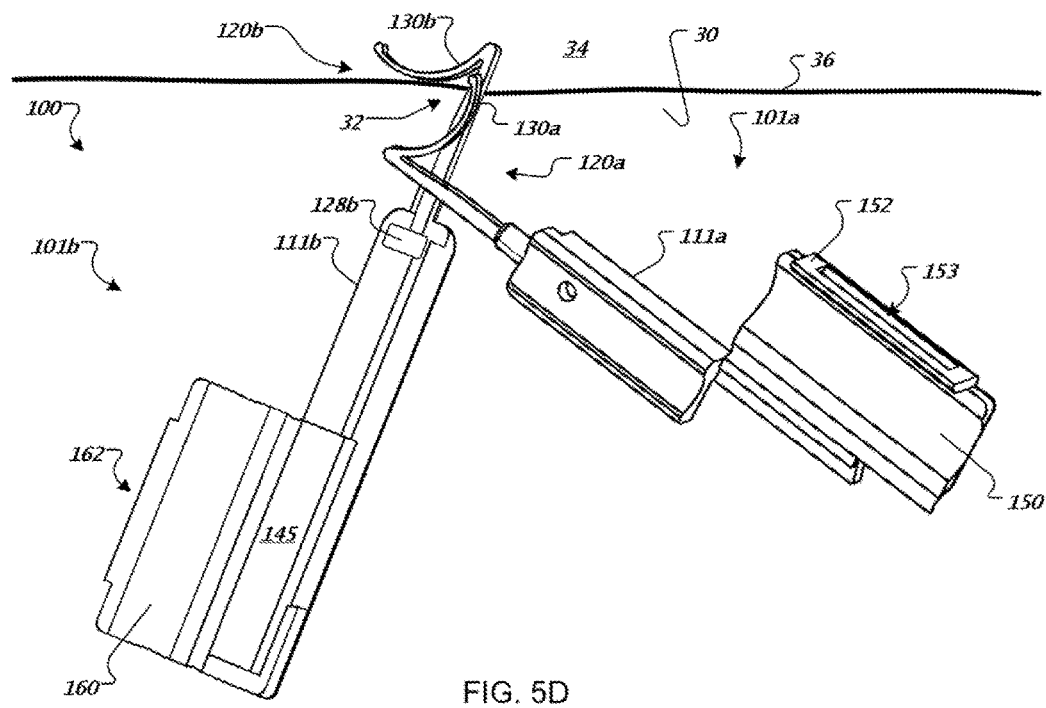

Referring now to FIGS. 5B-5D, after the portions 101a and 101b are separated from one another, the two portions 101a and 101b can be maneuvered so as to withdraw the anchors 120a and 120b (including the tines 130a and 130b) through the penetration point 32 of the skin 30. In the example illustrated in FIGS. 5B-D, the lower portion 101b can be held substantially fixed relative to the penetration point 32 while the upper portion 101a is maneuvered to individually remove the anchor 120a from the subcutaneous region 34. Removal in this manner can be used to limit the cross sectional area of the portion of the anchor 120a being withdrawn through the dermal layers 36, thus reducing the likelihood of damaging the surround skin tissue during removal of the anchor 120a (refer to FIG. 5D). Once the upper portion 101a is removed, the process can be repeated for the lower portion 101b.

Referring now to FIGS. 6A-6D, in use, the anchor system 100 can be used to retain a medical instrument 20, such as a catheter, in an operative position relative to a skin incision. In some embodiments, the penetration point 32 can be surgically opened in the skin 30, such that a catheter 20 can be inserted in the penetration point 32, through the subcutaneous region 34, and into a vein 40. After the catheter 20 is inserted, the anchor device 100 can be used to secure the catheter 20 relative to the penetration point 32.

Figure 6A:
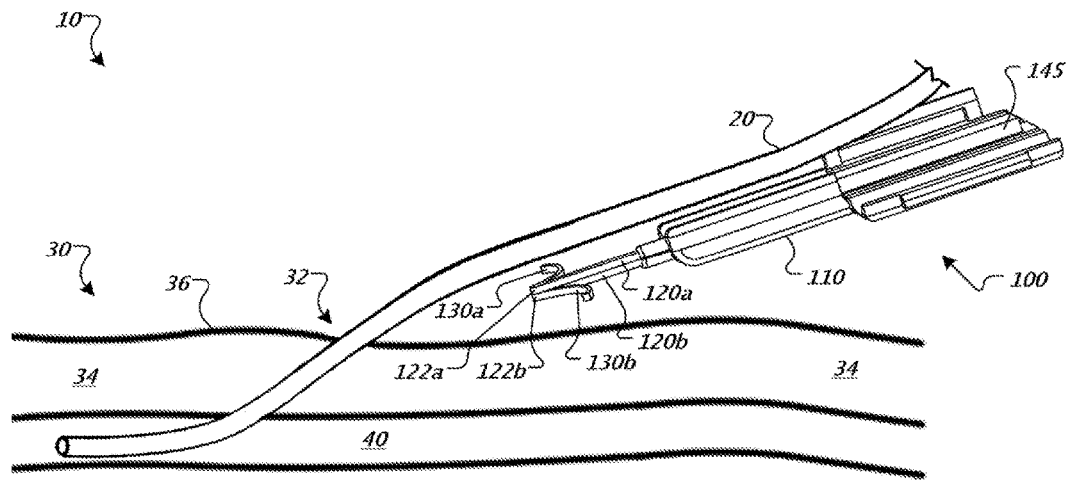
FIGS. 6A-6D are perspective views of the anchor device of FIG. 1, depicting its use in certain embodiments.

As shown in FIG. 6A, the anchor device 100 can be guided along the catheter 20 toward the skin 30 so that the anchor tips 122a-b approach the penetration point 32. The anchors 120a and 120b can be inserted into the patient's skin 30 through the penetration point 32 (e.g., through the same incision through which the catheter 20 was previously inserted) beginning with the tips 122a and 122b. As the anchors 120a and 120b are inserted into the skin 30, the tines 130a and 130b may flex to the contract position, as previously described in connection with FIG. 3B. By resiliently flexing against the anchor bodies 124a and 124b, the tines 130a and 130b can pass through the penetration point 32 in a way that reduces the likelihood of damage to the tissue surrounding the penetration point 32.

Figure 6B:
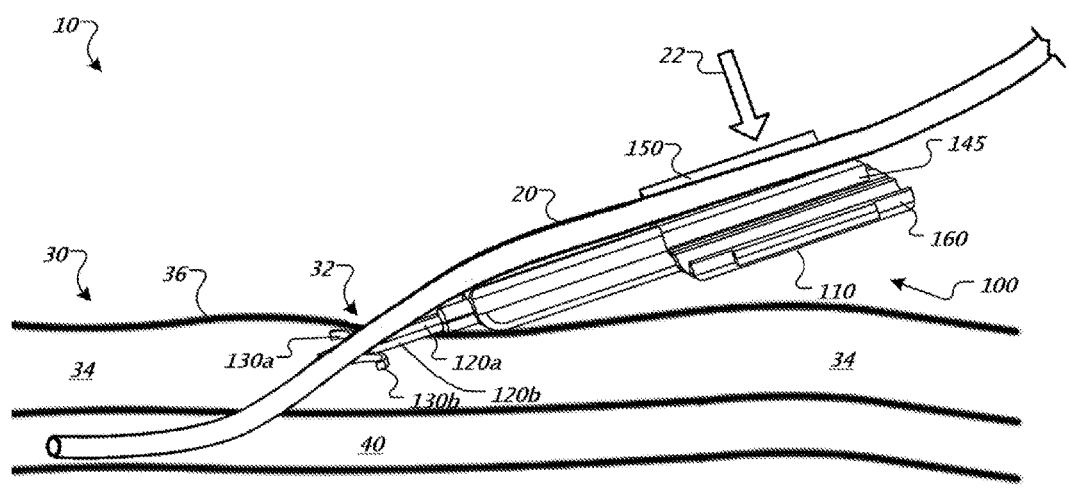

Referring now to FIG. 6B, after the anchors 120a and 120b penetrate the skin 30 so that the tines 130a and 130b pass into the subcutaneous region 34, the tines 130a and 130b can resiliently return toward an expanded position and thereby deploy in the subcutaneous region 34. The curved shape of the tines 130a and 130b can allow them to deploy adjacent to and abut the underside of the skin 30 to anchor the device 100 relative to the skin without tearing the dermal layers 36. To retain the catheter 20 in an operative position, the catheter can be positioned along the channel 112 of the retainer body and the adhesive pad 145, and the user may apply a force 22 to engage the catheter 20 with the adhesive surface of the pad 145. The retainer members 150 and 160 can then be transitioned to the closed configuration to thus retain the catheter 20 in a desired position relative to the penetration point 32 (as shown in FIG. 1). To reposition the catheter 20, the retention members 150 and 160 can be separated by disengaging the tabs 152 and 162, and the catheter 20 can be lifted from the adhesive pad 145 (while applying a stabilizing force to the anchor device 100). As the catheter 20 is no longer secured in place by the anchor device 100, it can be repositioned (advanced distally or withdrawn proximally) before being coupled once again to the adhesive pad 145 and the retention members 150 and 160 (as shown in FIG. 1).

Figure 6C:
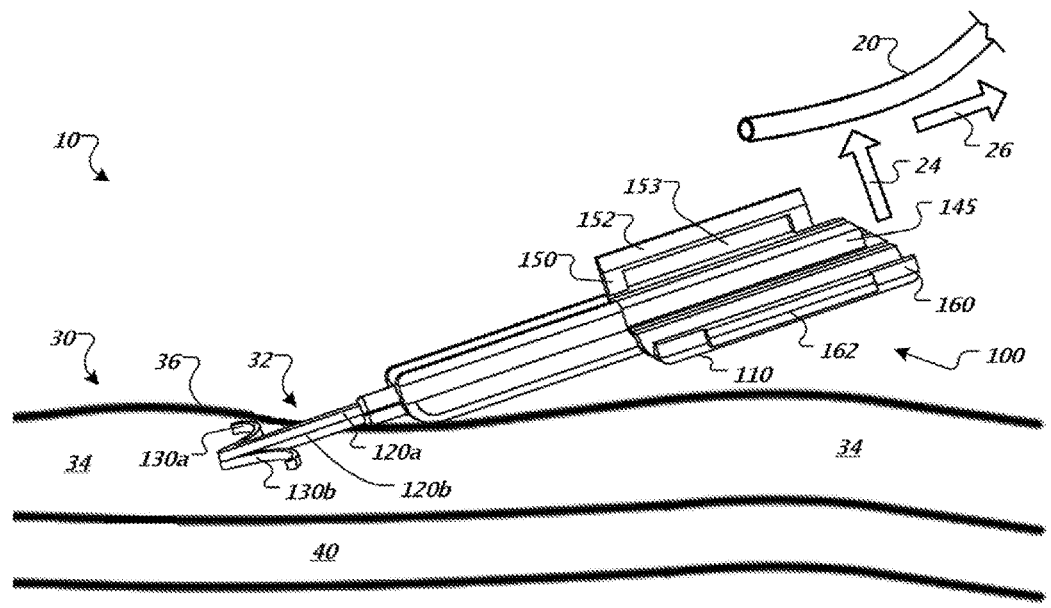

As shown in FIG. 6C, the catheter 20 can be withdrawn from the patient separately from the anchor device 100. In one example, after the catheter procedure is complete, the retention members 150 and 160 can be shifted to the opened configuration. The catheter 20 is then free to be peeled or lifted away from the adhesive pad 145 using a lifting force 24 (while applying a stabilizing force to the anchor device 100). After the catheter 20 is dissociated from the anchor device 100, the catheter 20 can be removed from the skin 30 by application of a withdrawal force 26 (while the anchor device 100 remains coupled to the skin 30).

Figure 6D:
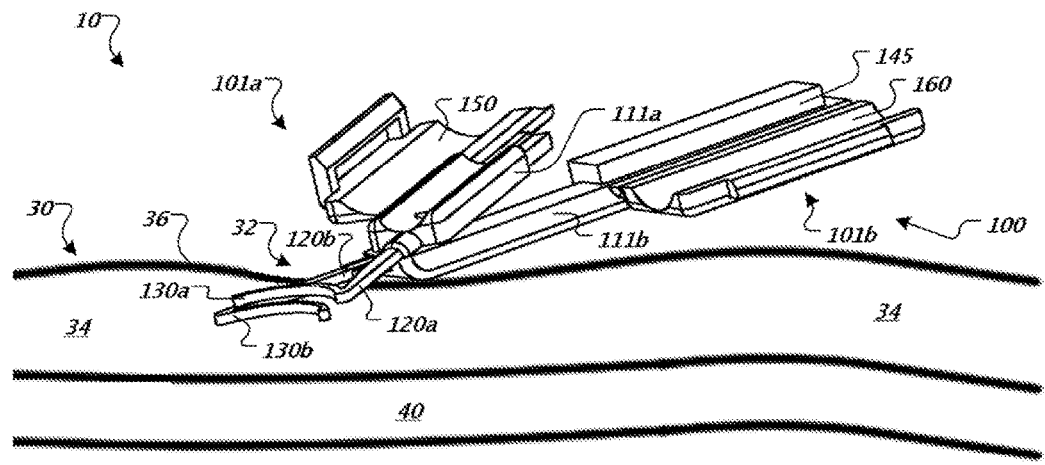

Referring now to FIG. 6D, the anchor device 100 can be removed from the patient's skin 30 in a manner that separately withdraws the anchors 120a and 120b. As described previously in connection with FIGS. 5A-5D, the anchor device 100 can be separated into multiple components so as to individually withdraw the anchors 120a and 120b from the skin 30. In the example depicted in FIG. 6D, the lower portion 101b can be held substantially fixed relative to the penetration point 32 while the upper portion 101a is maneuvered to individually remove the anchor 120a from the subcutaneous region 34. Once the upper portion 101a is removed, the process can be repeated for the lower portion 101b. In an alternative example, the upper portion 101a can be held substantially fixed relative to the penetration point 32 while the lower portion 101b is maneuvered to individually remove the anchor 120b from the subcutaneous region 34. Once the lower portion 101b is removed, the process can be repeated for the upper portion 101a. Such removal processes can be used to limit the cross sectional area of the portion of the anchor 120a or 120b being withdrawn through the dermal layers 36, thus reducing the likelihood of damaging the surround skin tissue during removal of the anchor 120a or 120b.

Referring now to FIGS. 7 and 8A-F, some embodiments of an anchor device 300 can employ different mechanisms for securing a medical instrument in a desired position. For example, the anchor device 300 can include a retainer body 310 having an instrument retention member 340 so as to apply a gripping force upon the medical instrument (e.g., a catheter in this embodiment). As such, the retainer body 310 can releasably engage a portion of catheter 20 (via the adjustable retention member 340) outside the patient's body. Similar to previously described embodiments, one or more flexible anchors 320a and 320b extend distally from the retainer body 310 for insertion in a subcutaneous region proximate a skin penetration point while the retainer body 310 is arranged outside the patient's body.

Figure 7:
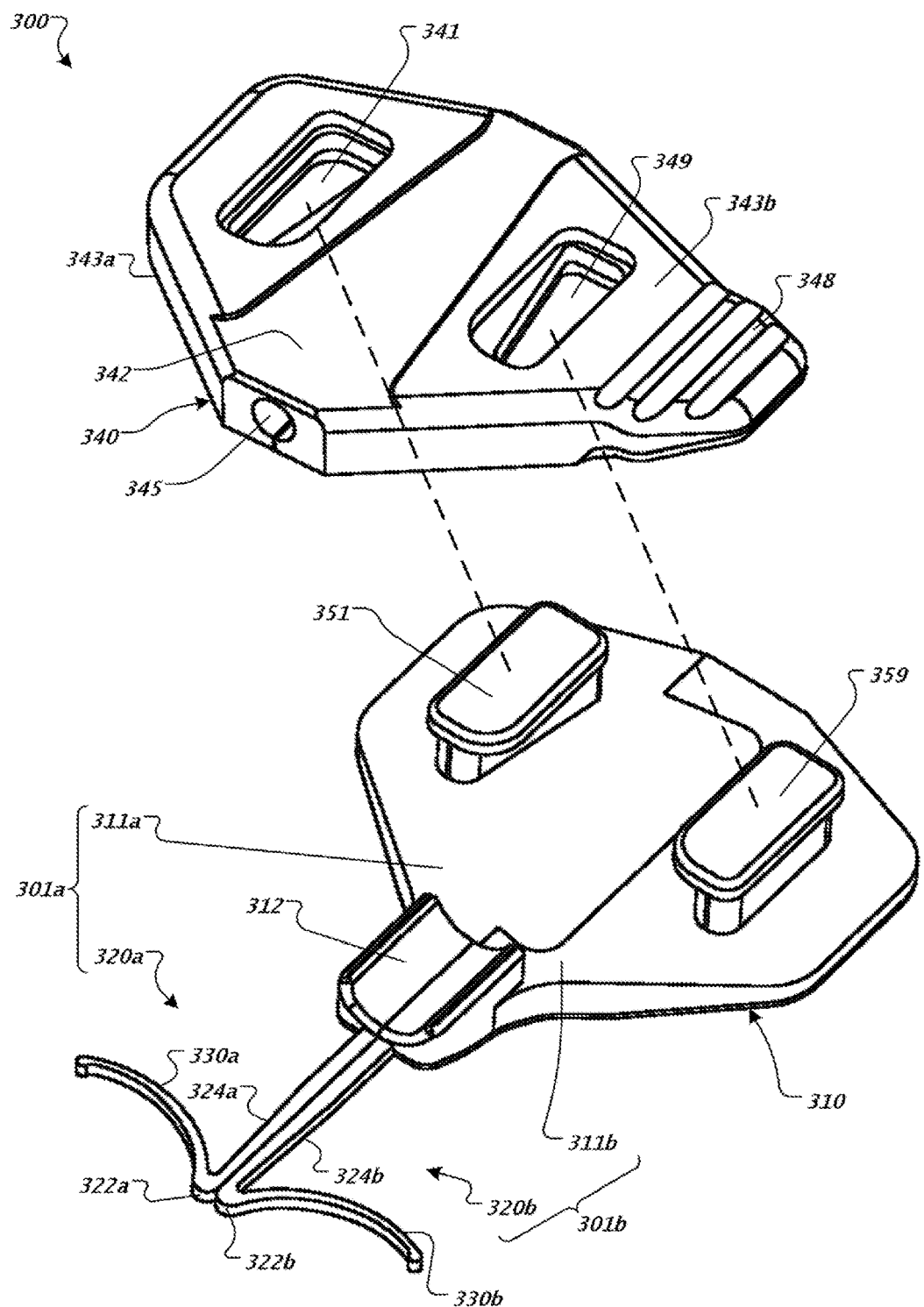
FIG. 7 is an exploded perspective view of an anchor device in accordance with some embodiments.

As shown in FIG. 7, in this embodiment, the retention member 340 may be removably attached to the retainer body 310 using one or more apertures 341 and 349 that mate with corresponding extensions 351 and 359. The retention member may comprise a flexible material, such as silicone or another biocompatible polymer material. For example, at least a flexible wall portion 342 may comprise silicone or another biocompatible polymer material so that a second region 343b can flexibly adjust relative to a first region 343a. In such circumstances, the apertures 341 and 349 can be forced over the corresponding extensions 351 and 359, and thereafter (if desired) one aperture 349 can be lifted from the retainer body 310 while the second aperture 341 remains secured to the retainer body 310 (as described below, for example, in connection with FIGS. 8A-C).

As previously described, the retention portion 340 can secure the catheter 20 (or another medical instrument) relative to a skin penetration point. For example, after the catheter 20 is delivered into the targeted vein 40 (or other bodily lumen) and after the anchors 320a and 320b are deployed in the subcutaneous region (proximate to the skin penetration point), the retention member 340 can be adjusted so that the catheter 20 is gripped inside a channel 345. In particular, the retention member 340 can be transitioned from an open configuration (shown in FIG. 8A) to a closed configuration (shown in FIG. 8B) to thereby secure the catheter 20 with the retention portion 340. The channel 345 may be at least partially defined by a wall comprising silicone or another flexible polymer that compresses against, and applies a holding force to, the outer surface of the catheter 20. As such, in some embodiments, the anchor device 300 can secure to catheter 20 without the use of an adhesive pad. It should be understood from the description herein that, in alternative embodiments, the anchor device 300 may include an adhesive pad to supplement the holding forces applied by the retention member 340.

Still referring to FIG. 7, the retainer body 310 may define a guide channel 312 that extends longitudinally from the retention portion 340 toward the anchors 320a and 320b. Similar to previously described embodiments, the guide channel 312 can be configured to abut with an outer surface of the catheter 20 or other medical instrument to be anchored by the device 300. For example, during installation of the anchor device 300, the guide channel 312 can be slid longitudinally along the catheter 20 so that the anchors 320a and 320b are directed toward a skin penetration point through which the catheter 20 passes. In addition, the channel 312 can be aligned with the gripping channel 345 defined by the retention member 340 when arranged in the closed configuration (FIG. 8B). As such, the catheter 20 can extend through the gripping channel 345 and along the guide channel 312 when the anchors 320a and 320b are deployed under the skin.

In use, the anchor device 300 can include features that facilitate separation from the catheter 20 and removal from the skin in a manner that reduces the likelihood of trauma to the skin surrounding penetration point. For example, the retention member 340 can include a tab 348 that can be readily grasped by a user to lift the second region 343b from the retainer body 310, thereby opening the channel 345 for removal of the catheter 20. After the retention portion 340 is shifted to the open configuration (FIG. 8C), the catheter 20 can be separated from the channel and moved independently from the anchor device 300 (e.g., to withdraw the catheter 20 from the patient while the anchor device 300 remains secured to the skin as shown in FIG. 8D). Moreover, similar to previously described embodiments, the anchor device 300 can include separable portions that can be disassembled prior to removal of the anchors 320a and 320b from the subcutaneous region. For example, in this embodiment, the anchor device 300 comprises an assembly of two pieces 301a and 301b (FIGS. 8E-F) that can separate from one another to facilitate removal of the tine 330b independent of the other tine 330a. Such a configuration permits the anchors 320a and 320b to be maneuvered in a manner that reduces the likelihood of causing damage to the skin during removal.

Referring now to FIGS. 8A-F, the anchor system 100 may retain the medical instrument, such as the catheter 20, in an operative position relative to a skin penetration point 32. In some embodiments, the penetration point 32 can be surgically opened in the skin 30, such that a catheter 20 can be inserted in the penetration point 32, through the subcutaneous region 34, and into a vein 40. After the catheter 20 is inserted, the anchor device 300 can be used to secure the catheter 20 relative to the penetration point 32. In particular, the anchors 320a-b may be deployed in the subcutaneous region under the skin (proximate to the skin penetration point) while the retainer body 310 remains outside the skin to secure with the catheter.

Figure 8A:
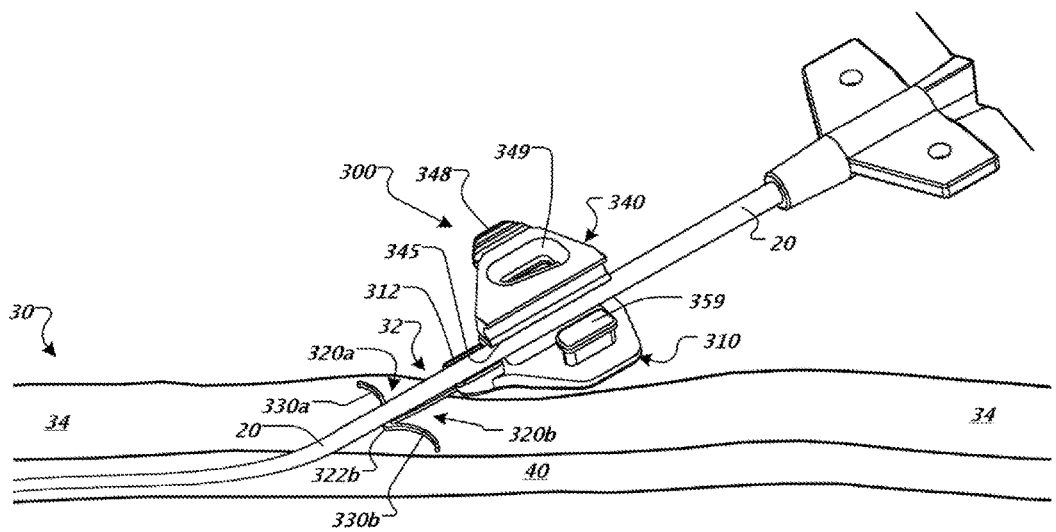
FIGS. 8A-8F are perspective views of the anchor device of FIG. 7, depicting its use in particular embodiments.
Figure 8B:
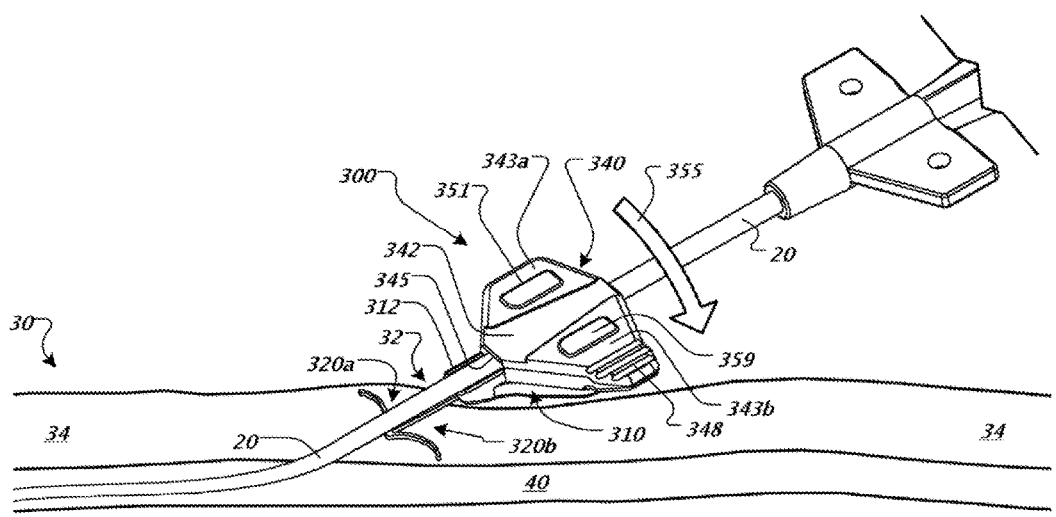

As shown in FIG. 8A, in some implementations, the anchor device 300 can be guided along the catheter 20 toward the skin 30 so that the anchor tips 322a-b (FIG. 7) approach the penetration point 32. In this example, the retention member 340 is removably attached to the retainer body 310 and is arranged in the open configuration. In these circumstances, the guide channel 312 an exposed portion of the gripping channel 345 can be guided longitudinally along the catheter 20 so that the anchors 320a and 320b are directed toward the skin penetration point 32. The anchors 320a and 320b can be inserted into the patient's skin 30 through the penetration point 32 (e.g., through the same opening through which the catheter 20 was previously inserted) beginning with the tips 322a and 322b. As the anchors 320a and 320b are inserted into the skin 30, the tines 330a and 330b may resiliently flex against the anchor bodies 324a and 324b (FIG. 7) to a contracted position (similar to previously described embodiments). As such, the tines 330a and 330b can pass through the penetration point 32 in a way that reduces the likelihood of damage to the tissue surrounding the penetration point 32. When the anchors 320a and 320b are collectively advanced through the penetration point 32, the tines 330a and 330b are moved beneath the dermal layers 36 (e.g., the dermis, the epidermis, etc.) of the skin 30. After the tines 330a and 330b reach the subcutaneous region 34, the tines 330a and 330b can return toward a curved shape (FIG. 7) and thereby deploy in the subcutaneous region 34. The anchors 320a and 320b may be designed such that the tines 330a and 330b include a curvature that abuts against the underside of the dermal layers 36 in a manner that reduces the likelihood of the tips 322a and 322b puncturing the underside of the dermal layers 36. As previously described, when the tines 330a and 330b are deployed in the subcutaneous region, the anchor device 300 can be secured to the patient without the retainer body 310 penetrating though the skin 30 of the patient and without necessarily requiring sutures or adhesive tapes bonded to the skin 30.

Referring now to FIG. 8B, the retention portion 340 can secure the catheter 20 relative to the skin penetration point 32 for a period of time in which the catheter 20 is used for treatment. For example, after the catheter 20 is delivered into the targeted vein 40 (or other bodily lumen) and after the anchors 320a and 320b are deployed in the subcutaneous region 34, the retention member 340 can be adjusted so that the catheter 20 is held inside the channel 345. In particular, the retention member 340 can be transitioned from the open configuration (FIG. 8A) to the closed configuration (shown in FIG. 8B) to thereby secure the catheter 20 with the retention portion 340. To retain the catheter 20 in this operative position, the user may grasp the tab 348 and apply a force 355 to adjust the second region 343b of the retention member 340 toward the mating extension 359. As previously described, the flexible wall 342 of the retention member 340 may act as a hinge-like connection between the second region 343b and the first region 343a so that the retention member 340 can be transitioned from the open configuration (FIG. 8A) to the closed configuration (shown in FIG. 8B). When transitioned to the closed configuration, the gripping channel 345 at least partially surrounds the catheter 20 and applies a holding force thereto. For example, the wall of the channel 345 may comprise silicone or another flexible polymer material that is configured to compress against the catheter's outer surface and thereby retain the catheter 20 in the selected position relative to the penetration point 32. To reposition the catheter 20, the retention member 340 can be adjusted to the open configuration (refer to FIG. 8A), and the catheter 20 can be repositioned (advanced distally or withdrawn proximally) before being coupled once again to the retention member 340 (as shown in FIG. 8B).

Figure 8C:
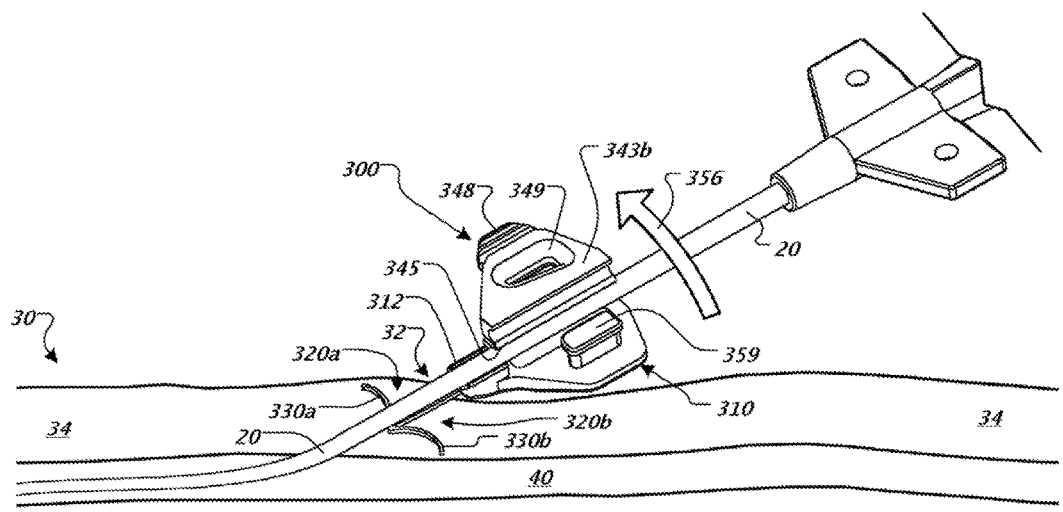
Figure 8D:
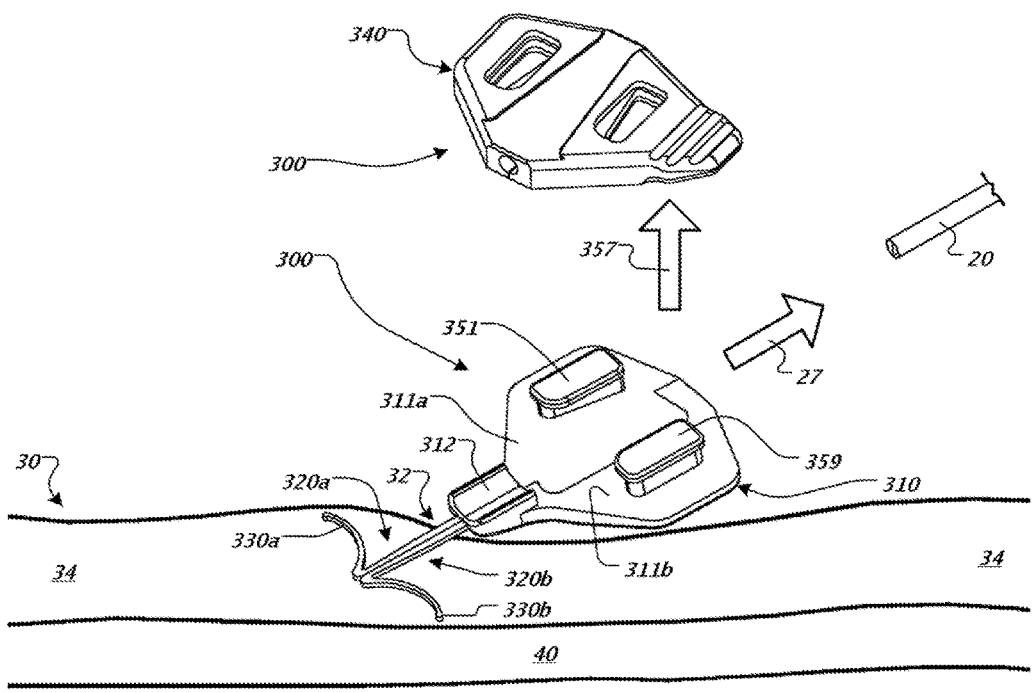

As shown in FIGS. 8C-D, the catheter 20 can be withdrawn from the patient separately from the anchor device 300. In this embodiment, after the catheter treatment is complete or the catheter 20 is otherwise ready to be removed, the retention member 340 can be shifted to the opened configuration (FIG. 8C). For example, the user may grasp the tab 348 and apply a force 356 (FIG. 8C) to adjust the second region 343b of the retention member 340 away the mating extension 359. Such adjustment of the retention member 340 can at least partially open the gripping channel 345 so that the catheter 20 can be moved independently from the anchor device 300. After the catheter 20 is dissociated from the anchor device 300, the catheter 20 can be removed from the skin 30 by application of a withdrawal force 27

(FIG. 8D). In this embodiment, the catheter 20 is withdrawn from the skin 30 while the anchor device 300 remains coupled to the skin 30 via the anchors 320a-b deployed in the subcutaneous region 34. The guide channel 312 of the retainer body 310 may provide guidance for the catheter 20 as it is withdrawn, thereby reducing the likelihood of tearing or damaging the skin around the penetration point 32. Optionally, the retention member 340 can be fully removed from the retainer body 310. For example, the retention member 340 can be lifted from the retainer body 340 (e.g., by application of a removal force 357) before the catheter 20 is withdrawn from the skin 30. As such, the catheter 20 can be withdrawn without interference from the retention member 340. Alternatively, the retention member 340 may remain in the open configuration (FIG. 8C) during withdrawal of the catheter 20.

Figure 8E:
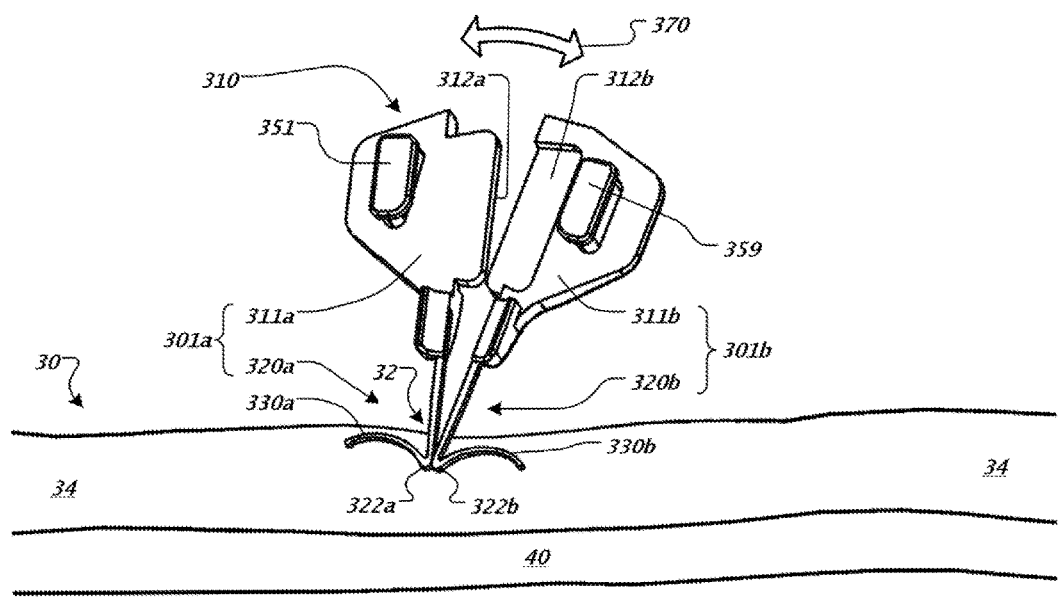
Figure 8F:
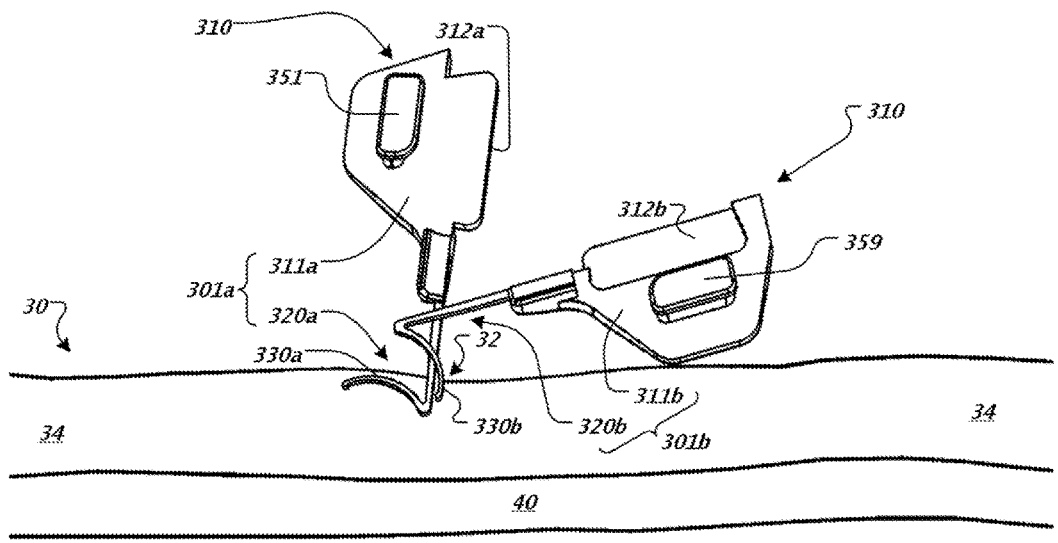

Referring now to FIGS. 8E-F, the anchor device 300 can be removed from the patient's skin 30 in a manner that separately withdraws the anchors 320a and 320b. As previously described, the anchor device 300 can be separated into multiple components so as to individually withdraw the anchors 320a and 320b from the skin 30. For example, as shown in FIG. 8E, a first portion 301a of the anchor device 300 can be separated from a second portion 301b before removing the anchors 320a and 320b from the subcutaneous region 34 under the skin 30. In this embodiment, the first portion 301a and the second portion 301b may be assembled together using a releasable adhesive coating along mating surfaces 312a and 312b. As such, the first portion 301a and the second portion 301b are coupled together (as the fully assembled anchor device 300) prior to insertion into the skin penetration point, yet the first portion 301a and the second portion 301b can be readily separated after the anchors 320a and 320b are deployed in the subcutaneous region 34. Accordingly, the anchors 320a and 320b (including the tines 330a and 330b) can collectively penetrate into the subcutaneous region 34 as part of the assembled device 100, and may be separately and individually withdrawn from penetration point 34 during the removal process.

Similar to previously described embodiments, at least a portion of the first portion 301a and the second portion 301b can comprise a polymer material (e.g., PVC, polypropylene, polystyrene, or the like). In such embodiments, first and second main bodies 311a-b of the retainer body 310 can be formed using a molding process in which each of the first and second main bodies 311a and 311b is overmolded around a portion of the associated anchor 320a or 320b. In some embodiments, the first portion 301a and the second portion 301b can be manufactured as two separate components that are later joined (e.g., by an adhesive bond, by ultrasonic spot welds, or the like) in a separable manner. In the embodiment depicted in FIG. 8E, the two portions 301a and 301b can be temporarily held in place while an adhesive is used to releasably bond the mating surfaces 312a-b. In some circumstances, the adhesive may be applied through an orifice (not shown in FIG. 8E) in the area proximate to the interfacing surfaces 312a and 312b. The adhesive employed in this assembly process can be a releasable adhesive that, during normal usage, retains the upper and lower portions 301a and 301b in the assembled state until the user desires to separate the interfacing surfaces 312a and 312b. At such time, the user may apply a separation force 370 (FIG. 8E) to divide the anchor device 300 into the two separate portions 301a and 301b. In addition or in the alternative to the releasable adhesive, the upper and lower portions 301a and 301b may include plastic spot welds, frangible portions or break lines, or other releasable structures at interfacing regions to releasably retain the portions 301a and 301b in the assembled state.

As shown in FIG. 8F, after the first and second portions 301a and 301b are separated from one another, the two portions 301a and 301b can be maneuvered so as to individually withdraw the anchors 320a and 320b (including the tines 330a and 330b) through the penetration point 32 of the skin 30. In this example, the first portion 301a can be held substantially stationary while the second portion 301b is maneuvered to individually remove the anchor 320b from the subcutaneous region 34. Removal in this manner can be used to limit the cross sectional area of the portion of the anchor 320b being withdrawn through the dermal layers 36, thus reducing the likelihood of damaging the surround skin tissue during removal of the anchor 320b. Once the second portion 301b is removed, the process can be repeated for the first portion 301a. In an alternative example, the second portion 301b can be held substantially stationary relative to the penetration point 32 while the lower portion 301b is maneuvered to individually remove the anchor 320a from the subcutaneous region 34. After the first portion 320a is removed, the process can be repeated for the second portion 301b. As previously described, such a removal process can be used to reduce the likelihood of damaging the surround skin tissue during removal of the anchor 320a or 320b.

Figure 9A:
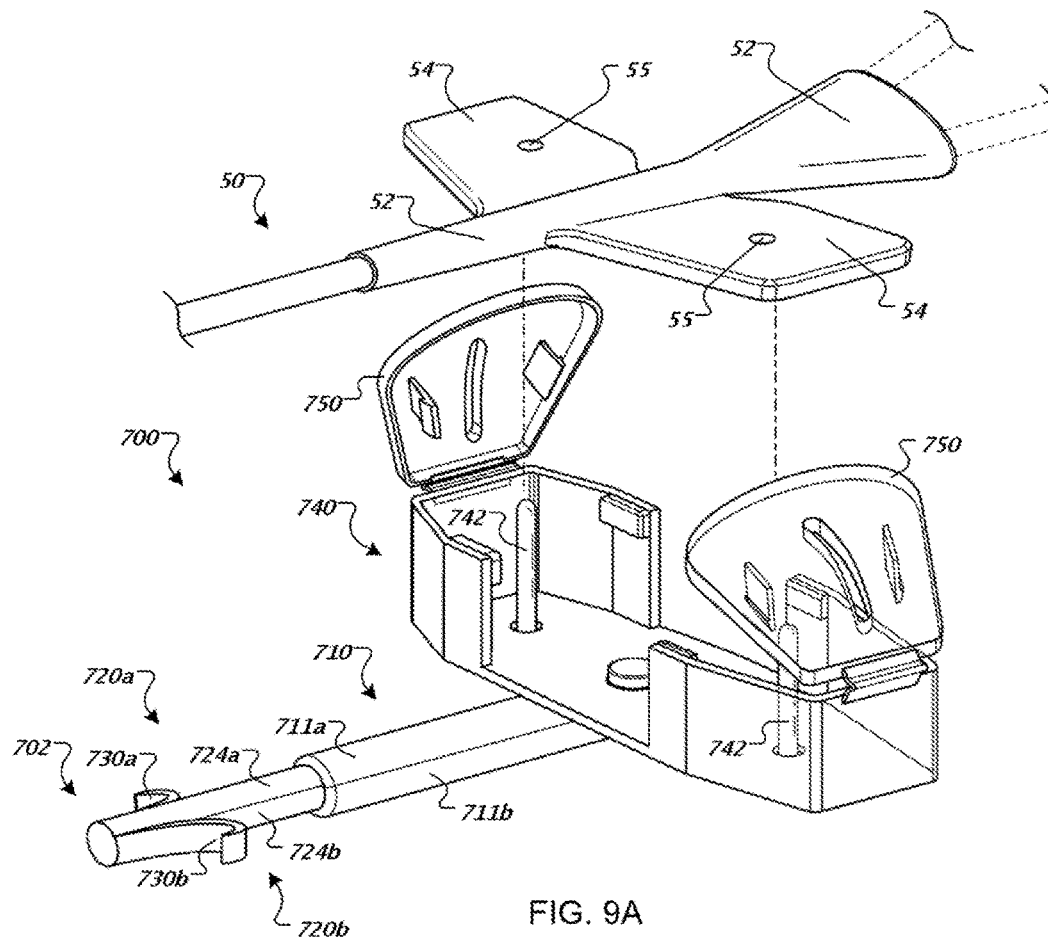
FIGS. 9A-9B are perspective views of an alternative embodiment of the anchor device having a portion that can retain a catheter hub.
Figure 9B:
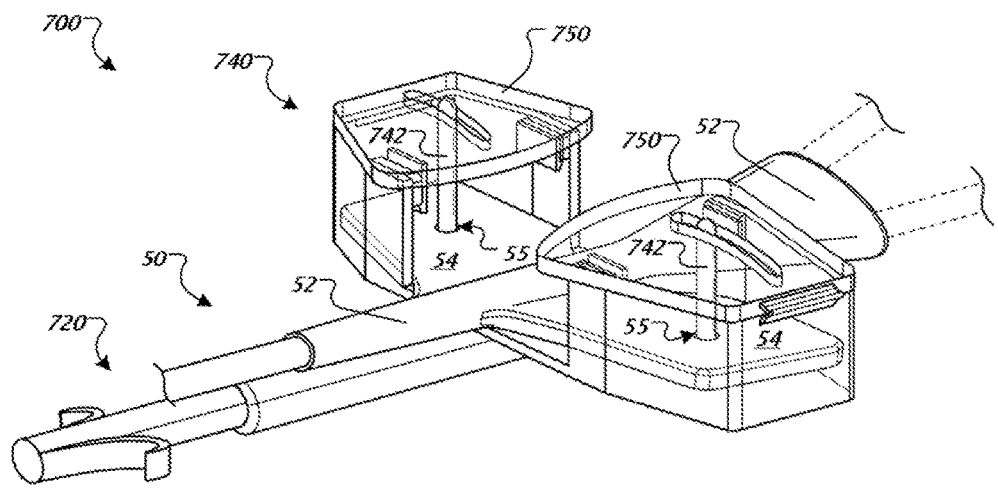

Referring now to FIGS. 9A-B, alternative embodiments of the anchor device can employ different mechanisms for securing medical instrument to the anchor device. For example, the anchor device 700 can include a retainer body 710, anchors 720a and 720b, and a retention portion 740 that can be used to secure a catheter 50 in an operative position relative to a skin incision. The catheter 50 can include a catheter hub 52 and wings 54 that mate with the retention portion 740 to secure the catheter 50 to the anchor device 700. In use, the catheter 50 can be inserted into a patient's skin through an incision (e.g., similar to the embodiment depicted in FIG. 6A) and into a targeted vein or bodily cavity. The anchor device 700 can be directed along the catheter 50 toward the skin so that the distal tip 702 (defined by the distal anchors 720a and 720b) approach the penetration point in the skin. As the anchor device 700 penetrates the skin, the flexible tines 730a and 730b can be stressed to flex against the anchor bodies 724a and 724b (similar to the embodiments described in connection with FIG. 3B), thereby reducing the likelihood of damaging the skin through which the anchor device 700 is being inserted. After the flexible tines 730a and 730b are arranged in the subcutaneous region under dermal layers, the tines 730a and 730b can resiliently deploy to an expanded position (similar to the position shown in FIG. 9A).

To secure the catheter 50 to the anchor device 700, the catheter hub 52 can be lowered into the retention portion 740 of the anchor device 700 such that the alignment pegs 742 enter orifices 55 in the catheter hub 52. After the catheter hub 52 is arranged within the retention portion 740 such that the pegs 742 mate with the orifices 55 the retention members 750 can be adjusted to a closed configuration (FIG. 9B). In such circumstances, the catheter 50 is coupled to the anchor device 700, which is anchored to the skin penetration point. After the catheter procedure is complete, the catheter 50 can be readily separated from the anchor device 700. For example, the retention members 750 can be adjusted to an opened configuration (FIG. 9A) so that the catheter hub 52 can lift from the anchor device 700 (while stabilizing the anchor device 700). After the catheter 50 is withdrawn, the anchor device 700 can be removed from the patient's skin in a manner that separately withdraws the anchors 720*a* and 720*b*. Similar to the embodiments previously in connection with FIGS. 5A-5D, the anchor device 100 can be separated into multiple components so as to individually withdraw the anchors 720*a* and 720*b* from the skin. In one example, a lower main body portion 711*b* can be held substantially fixed relative to the penetration point while an upper main body portion 711*a* (with the retention portion 740 coupled thereto) is maneuvered to individually remove the anchor 720*a* from the subcutaneous region. Once the upper main body portion 711*a* is removed, the process can be repeated for the lower main body portion 711*b*.

Referring now to FIG. 10, some embodiments of the anchor device can employ alternative features for securing the anchor device to the skin. For example, an anchor device 800 can include a hooked anchor 820 in which a portion of the anchor (tine 830) resides in the subcutaneous region 34 while the remaining portion of the anchor 820 (anchor body 810 and guide prongs 812) reside outside the skin 30. Similar to previously described embodiments, the anchor device 800 includes a retention portion 840 that is configured to engage a medical instrument 20 (such as a catheter) while an anchor 820 extends distally from the retention portion and into the same skin penetration point 32 as the catheter 20.

As shown in FIG. 10, the catheter 20 can be inserted into the patient's skin 30 through the penetration point 32. After insertion of the catheter 20, at least a portion of the anchor device 800 (e.g., a tine 830) can be inserted through the same penetration point 32 that the catheter 20 was previously inserted through. (It should be understood from the description herein that, in alternative embodiments, the anchor device 800 can be directed through the skin penetration point 32 before the catheter 20 is advanced therethrough.) As the tine 830 is inserted, the anchor device 800 can be pivoted to cause a distal tip 822 of the anchor 820 to pass into the skin along with the tine 830. As such, the top face 832 of the tine 830 can abut the underside of the skin 30 to retain the anchor device 800 in place. Thus, the tine 830 may serve as an atraumatic hook device that is arranged in the subcutaneous region. In this embodiment, the catheter 20 can be positioned between two guide prongs 812 of the anchor body 810 and on top of an adhesive pad (not shown) included in a retention portion 840. The adhesive pad in the retention portion 840 can be similar to the adhesive pad 145 previously described in connection with FIGS. 2A-B. After the catheter 20 is positioned between the two guides 812 and on top of the adhesive pad, retention members 850 and 860 can be transitioned from an open configuration to a closed configuration to secure the catheter 20 relative to the anchor device 800. As with previously described embodiments, the catheter 20 can be removed separately from the anchor device 800. After the catheter 20 is withdrawn from the skin 30, the anchor device 800 can be manipulated to pivot the anchor 820 and slide the tine 830 out of the skin 30 in a manner that reduces the likelihood of damage to the surrounding skin tissue.

Figure 11A:
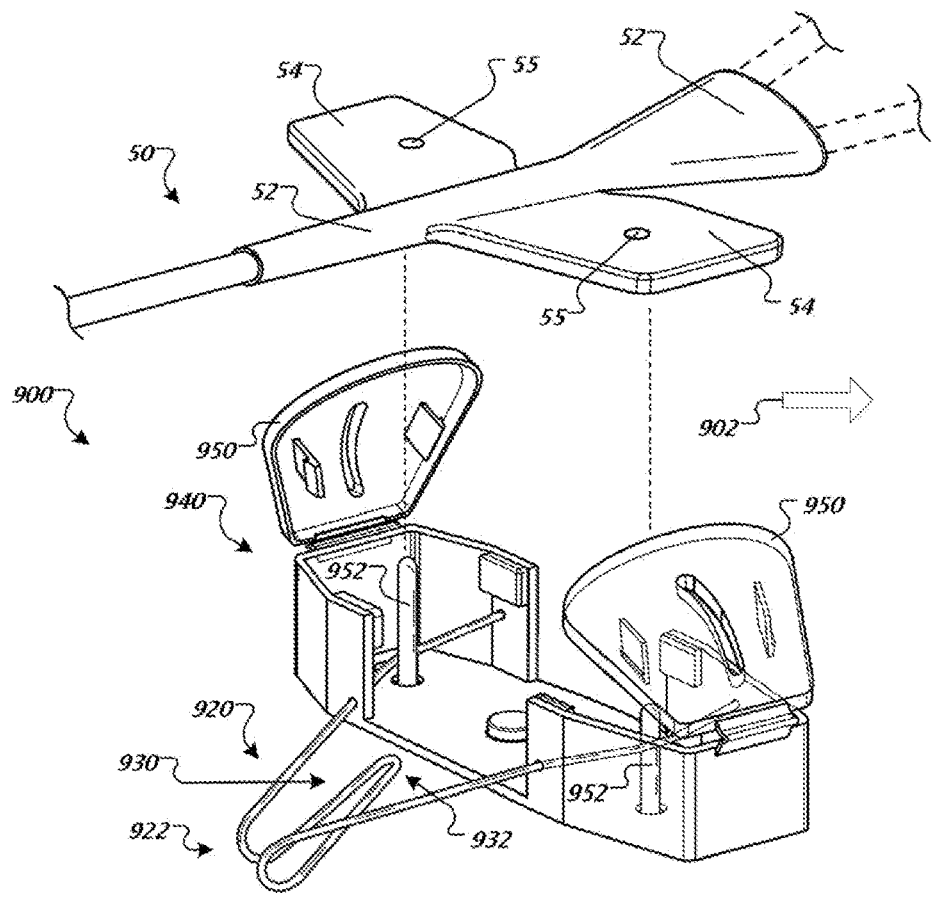
FIGS. 11A-11B are perspective views of an alternative embodiment of the anchor device having a bent-wire anchor and a portion that can retain a catheter hub.
Figure 11B:
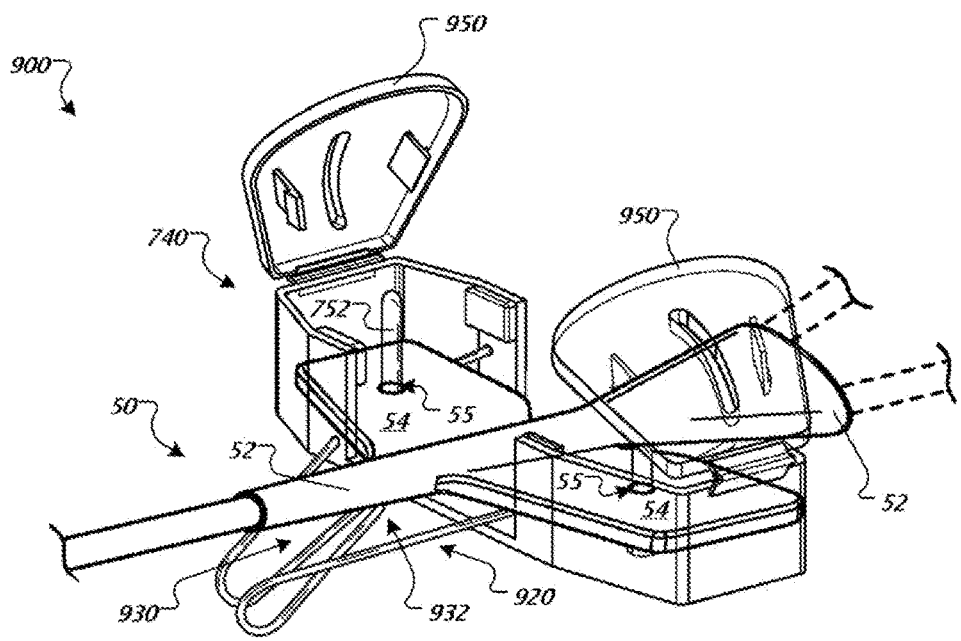

Referring now to FIGS. 11A-11B, alternate embodiments of an anchor device 900 can include an alternative anchor configuration to secure the anchor device to the skin penetration point. Similar to previously described embodiments, the anchor device 900 includes a retention portion 940 that is configured to engage a medical instrument 50 (such as a catheter) while an anchor 920 extends distally from the retention portion and into the same skin penetration point 32 as the catheter 50. In this example, the anchor device 900 includes a hooked anchor 920 in which a portion of the anchor (a tine configured as arm 932) resides in the subcutaneous region 34 while another portion of the anchor 920 extends outside the skin 30 to couple with the retention portion 940. The retention portion 740 can mate with a catheter hub 52 of the catheter 50 to secure the catheter 50 in a desired position relative to the skin penetration point.

In use, the catheter 50 can be inserted into a patient's skin through an incision (e.g., similar to the embodiment depicted in FIG. 6A) and into a targeted vein or bodily cavity. The anchor device 900 can be directed toward the skin so that the arm 932 of the anchor reaches the skin penetration point. The anchor device 900 can be directed through the skin penetration point before or after the catheter 50 is advanced therethrough. As the arm 932 is inserted, the anchor device 900 can be pivoted to cause a distal tip 922 of the anchor 920 to pass into the skin along with the arm 932. As such, the arm 932 can abut the underside of the skin to retain the anchor device 900 in place. Similar to embodiments previously described in connection with FIG. 10, the arm 932 of the anchor 920 may serve as an atraumatic hook device that is arranged in the subcutaneous region.

To secure the catheter 50 to the anchor device 900, the catheter hub 52 can be lowered into the retention portion 940 of the anchor device 900 such that the alignment pegs 952 enter orifices 55 in the catheter hub 52. After the catheter hub 52 is arranged within the retention portion 940 such that the pegs 952 mate with the orifices 55, the retention members 950 can be adjusted to a closed configuration (FIG. 11B). In such circumstances, the catheter 50 is coupled to the anchor device 900, which is anchored to the skin penetration point. After the catheter procedure is complete, the catheter 50 can be readily separated from the anchor device 900 by adjusting the retention members 750 to an opened configuration (FIG. 11A) and lifting the catheter hub 52 away from the anchor device 900. After the catheter 50 is withdrawn, the anchor device 900 can be manipulated to pivot the anchor 920 and slide the arm 932 out of the skin in a manner that reduces the likelihood of damage to the surrounding skin tissue.

A number of embodiments of the invention have been described. Nevertheless, it will be understood that various modifications may be made without departing from the spirit and scope of the invention. Accordingly, other embodiments are within the scope of the following claims.

What is claimed is:

1. A method of anchoring a medical instrument, comprising:
   advancing the medical instrument through a skin penetration point of a patient's body, the medical instrument comprising an external portion configured to reside external to the skin penetration point when the medical instrument is inserted into the skin penetration point;
   engaging the external portion of the medical instrument with a retainer device by adjusting a flexible portion of the retainer device from a first configuration to a second configuration, the retainer device comprising:
      a retainer body comprising the flexible portion;
      a first anchor comprising a first external shaft portion, the first anchor extending distally from a distal end of the retainer body and toward the skin penetration point when the medical instrument is inserted into the skin penetration point and engaged with the retainer body; and
      a second anchor comprising a second external shaft portion, the second anchor extending distally from the distal end of the retainer body and toward the skin penetration point when the medical instrument is inserted into the skin penetration point and engaged with the retainer body, the first and second external shaft portions positionable side-by-side during insertion and movable relative to one another during removal from a subcutaneous region; and inserting the first and second anchors through the skin penetration point so that at least a portion of each of the first and second anchors is deployed in the subcutaneous region proximate the skin penetration point, wherein the first external shaft portion of the first anchor and the second external shaft portion of the second anchor are positioned side-by-side during insertion through the skin penetration point.

2. The method of claim 1, wherein the first and second anchors are inserted through the skin penetration point so that the at least a portion of each of the first and second anchors is deployed in the subcutaneous region while the entire retainer body is arranged externally of the skin penetration point.

3. The method of claim 1, wherein the first anchor comprises a first flexible tine coupled to the first external shaft portion and the second anchor comprises a second flexible tine coupled to the second external shaft portion, and the first flexible tine of the first anchor is configured to extend outwardly away from the second flexible tine of the second anchor when the flexible tines are deployed in the subcutaneous region.

4. The method of claim 3, comprising inserting the first and second flexible tines through the skin penetration point while the skin penetration point is occupied by the medical instrument.

5. The method of claim 1, comprising engaging the external portion of the medical instrument with the retainer device while the medical instrument is occupied within the skin penetration point.

6. The method of claim 5, wherein inserting the first and second anchors through the skin penetration point occurs before engaging the external portion of the medical instrument with the retainer device.

7. The method of claim 1, wherein the retainer body comprises a cap member and a lower body member, the cap member releasably engageable with the lower body member via an engagement structure of the cap member configured to mate with a corresponding engagement structure of the lower body member.

8. The method of claim 7, comprising adjusting the retainer body from the first configuration to the second configuration while the cap member is engaged with the lower body member.

9. The method of claim 1, wherein the retainer body comprises first and second body portions, and the flexible portion comprises a hinged connection between the first and second body portions.

10. The method of claim 9, comprising separating the first body portion from the second body portion during removal of the first and second anchors from the skin penetration point.

11. The method of claim 1, wherein the first configuration is an open position in which the medical instrument is movable independent from the retainer body and the second configuration is a closed position in which the medical instrument is engaged by the retainer body.

12. The method of claim 1, wherein the retainer body comprises a cap member comprising the flexible portion.

13. The method of claim 1, comprising removing the first anchor from the skin penetration point independent from the second anchor.

14. The method of claim 1, wherein the retainer body comprises a catheter receiving channel that extends along a longitudinal axis, and the first and second external shaft portions of the first and second anchors extend generally parallel to the longitudinal axis.

15. A method of anchoring a medical instrument, comprising:

advancing the medical instrument through a skin penetration point of a patient's body, the medical instrument comprising an external portion configured to reside external to the skin penetration point when the medical instrument is inserted into the skin penetration point;

engaging the external portion of the medical instrument with a retainer device by adjusting a flexible portion of the retainer device from a first configuration to a second configuration, the retainer device comprising:

a retainer body comprising the flexible portion;

a first anchor comprising a first external shaft portion and a first flexible tine coupled to the first external shaft portion, the first anchor extending distally from a distal end of the retainer body and toward the skin penetration point when the medical instrument is inserted into the skin penetration point and engaged with the retainer body; and a second anchor comprising a second external shaft portion and a second flexible tine coupled to the second external shaft portion, the second anchor extending distally from the distal end of the retainer body and toward the skin penetration point when the medical instrument is inserted into the skin penetration point and engaged with the retainer body, the first and second external shaft portions positionable side-by-side during insertion and movable relative to one another during removal from a subcutaneous region; and inserting the first and second anchors through the skin penetration point so that at least the first and second flexible tines and at least portions of each of the first and second external shaft portions are deployed in the subcutaneous region proximate the skin penetration point, wherein the first external shaft portion of the first anchor and the second external shaft portion of the second anchor are positioned side-by-side during insertion through the skin penetration point.

16. The method of claim 15, comprising simultaneously inserting the first and second flexible tines through the skin penetration point while the skin penetration point is occupied by the medical instrument.

17. The method of claim 16, comprising engaging the external portion of the medical instrument with the retainer device after the first and second flexible; tines are deployed in the subcutaneous region.

18. The method of claim 17, wherein the retainer body comprises first and second body portions, and the flexible portion comprises a hinged connection between the first and second body portions.

19. The method of claim 18, comprising separating the first body portion from the second body portion during removal of the first and second anchors from the skin penetration point.

20. The method of claim 19, wherein the first flexible tine is configured to extend outwardly away from the second flexible tine when the flexible tines are deployed in the subcutaneous region.

* * * * *

UNITED STATES PATENT AND TRADEMARK OFFICE
CERTIFICATE OF CORRECTION

PATENT NO. : 10,471,236 B2
APPLICATION NO. : 15/897908
DATED : November 12, 2019
INVENTOR(S) : Michael S. Rosenberg et al.

It is certified that error appears in the above-identified patent and that said Letters Patent is hereby corrected as shown below:

In the Claims

In Claim 17, delete "flexible;" and insert -- flexible --, therefore.

Signed and Sealed this
Fourteenth Day of January, 2020

Andrei Iancu
*Director of the United States Patent and Trademark Office*